(12) United States Patent
Bunge et al.

(10) Patent No.: US 10,610,617 B2
(45) Date of Patent: Apr. 7, 2020

(54) METHOD FOR COATING A MEDICAL IMPLANT

(71) Applicants: BIOTRONIK SE & CO. KG, Berlin (DE); ALBERT-LUDWIGS-UNIVERSITAET FREIBURG, Freiburg (DE)

(72) Inventors: Andreas Bunge, Leipzig (DE); Michael Bergmann, Freiburg (DE); Loic Ledernez, Freiburg (DE); Alexander Borck, Heidesee (DE); Gerald Urban, Freiburg (DE)

(73) Assignees: BIOTRONIK SE & Co. KG, Berlin (DE); Albert-Ludwigs-Universitat Freiburg, Freiburg (DE)

( * ) Notice: Subject to any disclaimer, the term of this patent is extended or adjusted under 35 U.S.C. 154(b) by 104 days.

(21) Appl. No.: 15/512,740

(22) PCT Filed: Oct. 21, 2015

(86) PCT No.: PCT/EP2015/074358
§ 371 (c)(1),
(2) Date: Mar. 20, 2017

(87) PCT Pub. No.: WO2016/062763
PCT Pub. Date: Apr. 28, 2016

(65) Prior Publication Data
US 2017/0296709 A1    Oct. 19, 2017

(30) Foreign Application Priority Data

Oct. 23, 2014 (DE) .................. 10 2014 221 587
Oct. 23, 2014 (DE) .................. 10 2014 221 588

(51) Int. Cl.
| | | |
|---|---|---|
| *A61L 31/10* | (2006.01) |
| *A61L 27/44* | (2006.01) |
| *A61L 27/50* | (2006.01) |
| *A61L 31/12* | (2006.01) |
| *A61L 27/56* | (2006.01) |
| *A61L 31/16* | (2006.01) |
| *A61L 27/34* | (2006.01) |
| *A61L 31/14* | (2006.01) |
| *A61L 27/54* | (2006.01) |
| *A61L 27/30* | (2006.01) |
| *A61L 27/36* | (2006.01) |

(52) U.S. Cl.
CPC ............ *A61L 27/44* (2013.01); *A61L 27/303* (2013.01); *A61L 27/34* (2013.01); *A61L 27/3616* (2013.01); *A61L 27/446* (2013.01); *A61L 27/505* (2013.01); *A61L 27/507* (2013.01); *A61L 27/54* (2013.01); *A61L 27/56* (2013.01); *A61L 31/10* (2013.01); *A61L 31/125* (2013.01); *A61L 31/128* (2013.01); *A61L 31/143* (2013.01); *A61L 31/146* (2013.01); *A61L 31/16* (2013.01); *A61L 2300/102* (2013.01); *A61L 2300/406* (2013.01); *A61L 2300/606* (2013.01); *A61L 2400/12* (2013.01); *A61L 2400/18* (2013.01); *A61L 2420/02* (2013.01)

(58) Field of Classification Search
CPC ......... A61L 2300/102; A61L 2300/406; A61L 2300/606; A61L 2400/12; A61L 2400/18; A61L 2420/02; A61L 27/303; A61L 27/34; A61L 27/3616; A61L 27/44; A61L 27/446; A61L 27/505; A61L 27/507; A61L 27/54; A61L 27/56; A61L 31/10; A61L 31/125; A61L 31/128; A61L 31/143; A61L 31/146; A61L 31/16
See application file for complete search history.

(56) References Cited

U.S. PATENT DOCUMENTS

| | | | | |
|---|---|---|---|---|
| 2012/0088990 A1* | 4/2012 | Bunge | ............... | A61B 5/14503 600/309 |
| 2012/0107592 A1* | 5/2012 | Vasilev | ............. | A61F 13/00017 428/220 |

FOREIGN PATENT DOCUMENTS

| | | | | |
|---|---|---|---|---|
| EP | 2151253 A1 | 2/2010 | | |
| EP | 2252410 B1 | 12/2011 | | |
| WO | WO 00/69951 | * 5/2000 | ............... | C08J 9/00 |
| WO | 00/69951 A2 | 11/2000 | | |

OTHER PUBLICATIONS

Gevers et al. (Journal of Membrane Science: 281 (2006) 741-746) (Year: 2006).*
Harris et al. (Biomaterials 25 (2004) 4135-4148) (Year: 2004).*
Safe Drinking Water Foundation (Ultrafiltration, Nanofiltration and Reverse Osmosis https://www.hinesburg.org/water-project/safewaterdotorg-info-nano-and-ultrafiltration-reverse-osnnosis.pdf 2015) (Year: 2015).*

(Continued)

*Primary Examiner* — Anna R Falkowitz

(74) *Attorney, Agent, or Firm* — Greer, Burns & Crain, Ltd.; Steve P. Fallon

(57) ABSTRACT

A method for coating a medical implant applies at least one coating to at least one surface of the implant by plasma polymerization. The implant has pores sized in the nanometer range. The method stabilizes the pores. The plasma polymerization is conducted in the presence of a coating gas and oxygen. A coating parameter can be selected so that a rough surface of the implant is coated. An implant includes a membrane having pores sized in the nanometer range. A surface of the implant is at least partially coated with a plasma polymer. The interior of the pores is uncoated.

19 Claims, 20 Drawing Sheets

(56) References Cited

OTHER PUBLICATIONS

Hansen (the Bell Jar: Some Vacuum Basics (2008) http://www.belljar.net/basics.htm) (Year: 2008).*
Gevers, Lieven, E.M., et al., "Optimisation of a lab-scale method for preparation of composite membranes with a filled dense top-layer", Journal of Membrane Science, vol. 281, (2006), pp. 741-746.
Harris, L.G., et al., "Staphylococcus aureus adhesion to titanium oxide surfaces coated with non-functionalized and peptide-functionalized poly(L-lysine)-grafted-poly(ethylene glycol) copolymers", Biomaterials, vol. 25, (2004), pp. 4135-4148.
Losic, Dusan, et al., "Surface modification of nanoporous alumina membranes by plasma polymerization", ganotechnology, vol. 19, (2008), 245704, (7 pages).
Madkour, Ahmad, E., et al., "End-functionalized ROMP polymers for Biomedical Applications", Macromolecules, vol. 43, No. 10, May 25, 2010, pp. 4557-4561.
Tsai, Ching-Yuan, et al., "Surface Modification of Polypropylene Membrane by RF Methane/Oxygen Mixture Plasma Treatment", Japanese Journal of Applied Physics, vol. 50, (2011), pp. O8KA02-1-O8KA02-7.
Psei, Maria, et al. "Notificaiton of Transmittal of the International Search Report and the Written Opinion of the International Searching Authority, or the Declaration", Patent Cooperation Treaty No. PCT/EP2015/074358, European Patent Office as International Searching Authority, International Search Completed Nov. 17, 2015, International Search Report dated Nov. 25, 2015, 12 pages.
Riederer, Florian, "European Search Report", European Patent Application No. EP 14 19 0140, dated Apr. 7, 2015, (9 pages).

* cited by examiner

METHOD FOR COATING A MEDICAL IMPLANT

TECHNICAL FIELD

The invention relates to a method for coating a medical implant and to coating medical implants.

BACKGROUND

Implants are used in medicine, which are introduced permanently or at least for an extended period into an animal body and/or a human body to fulfill replacement functions. Numerous implants and systems may be considered for this purpose, such as biosensors, dialysis tubing, drug delivery systems, pacemakers, cardiac implants, implants for joint replacement, vascular prostheses or stents.

Implants are typically identified by the organism as being foreign after they are introduced in the body. In response to the artificial surfaces, proteins aggregate thereon only a short time after implantation due to non-specific protein adsorption. These adsorbed proteins at least partially lose the three-dimensional structures thereof and serve as anchoring substrates for the aggregation of cells. These proteins are recognized by cells (including by thrombocytes, if the implant is introduced into the blood stream). This triggers non-defined cell coverage and/or an extracellular matrix of protein fibers (such as collagen) on the surface of the implant. This process is generally referred to as a foreign body reaction or fouling. Quite frequently, even collagen-containing encapsulation of the implant can be observed.

Implants encapsulated in tissue may lose the function thereof (for example, an analyte is able to reach the biosensor only partially, with time delay, or not at all, pores of a polymer membrane of the biosensor become clogged, or a stimulus threshold for stimulating implants changes). Moreover, encapsulated implants are more difficult to explant (for example, defective stimulation electrodes are not explanted, but remain in the body). In the human body, the described protein adsorption furthermore acts as an initiator for a foreign body reaction and may ultimately also lead to the formation of encapsulations and thrombi, which can be life-threatening for the patient.

However, this is not the only severe risk for the patient. Despite extensive progress in surgical medicine, infections following the introduction of a sterilized implant still represent very frequent complications. The adhesion of microorganisms (adhesion phase) always marks the beginning of an implant infection following implantation. The surface morphology and the physicochemical properties of the implant material are relevant for the adhesion of organisms to the implant surfaces. Binding is favored if biopolymers (in particular polysaccharides) have already adhered to the surface. Reproduction of the microorganisms results in extensive, and later explosive, three-dimensional colonization of the surface. The simultaneous bacterial synthesis of epoxy polysaccharides and other organic molecules causes the bacteria to be sheathed by a mucus-like matrix, which is referred to as a biofilm. If the biofilm is formed across a large area, the body's own antibacterial mechanisms as well as antibiotics are no longer able to prevent the organisms from spreading further on the implant and throughout the entire body. At times, this may result in life-threatening situations. An infection manifests itself to the patient by necrosis, chronic inflammations, abscesses, endocarditis, myocarditis, sepsis and the like. As many as one in five patients suffering from such infection dies within one year of becoming infected.

The bacteria causing the infection are usually introduced during implantation/revision surgery and cause either acute or latent infections. Staphylococci are responsible for these infections in 60 to 80% of cases (*S. epidermis* and *S. aureus*), but other bacteria such as *E. coli* also play a role. If typical antibiotic-(multi)resistant nosocomial microbes are introduced into the body, the situation can become particularly critical. If an infection involving biofilms occurs, it is frequently necessary to replace the implant with a new implant (referred to as revision surgery), since an antibiotics therapy alone is generally not sufficient. From the point of view of health care costs, infections pose a major problem; the administration of antibiotics alone may result in costs of approximately 5000 euros in certain situations, to which the costs for the new implant and the implantation are added. Infections of the pacemaker pocket and/or of an electrode system can occur with an incidence rate of up to 12%, for example. Often times a single implant replacement does not suffice since biofilms represent a focus of continuously recurring infections.

If a combination of an encapsulation of the implant and a bacterial infection occurs, the patient's immune system is substantially defenseless since immune cells are not able to penetrate to the bacterial center. This is particularly critical when replacing the implant (for example, when the service life of the implant is exhausted). During these replacements, the implant is typically introduced into the capsule formed by the previous implant. In general, this automatically also results in bacteria being introduced into the body and the collagen capsule. An infection of what is known as the pacemaker pocket generally forms just the starting point. The infection can then spread along the electrodes that are anchored in the heart. Medical procedures to disrupt or even remove the collagen-containing capsule are complex and presumably associated with a longer healing process.

In particular in view of an aging and multimorbid population, the complications that occur are particularly critical, and more implant replacements are needed at the same lifetime of the implants given patients' higher life expectancy. Multimorbidities, which is to say the simultaneous occurrence of multiple chronic diseases in a patient, pose additional risks. The risk of infection of patients with pacemakers/defibrillators/CRT devices is increased, for example, if they suffer from diabetes and renal insufficiency.

It is therefore of great importance to improve the compatibility of implants and substantially minimize a defense reaction of the patient's body against the implant. An improvement in the compatibility of visual prostheses, such as contact lenses, that can be attached externally to the body is known to be achievable by way of a coating, applied by way of plasma polymerization (Evaluation of plasma polymer-coated contact lenses by electrochemical impedance spectroscopy. Weikart C M, Matsuzawa Y, Winterton L, Yasuda H K. J Biomed Mater Res. 2001 Mar. 15; 54(4): 597-607.). The coating protocols established for this purpose, however, are only successful on smooth surfaces. On these, however, the adhesion of the coating, such as under mechanical load, is often not sufficient. Such coatings are consequently not suitable for implants that are introduced into the body, especially for long-term use. Moreover, a plurality of implant surfaces do not have smooth surfaces, whereby the above-described coating protocols cannot be readily employed.

In addition, a number of surface modifications of the implant surface are known, which are intended to prevent colonization with bacteria (Implant infections: a haven for opportunistic bacteria. Schierholz J M, Beuth J., J Hosp Infect. 2001 October; 49(2):87-93. Review.). It is primarily antibiotically active molecules that bind to the surface. This is possible covalently by way of spacers; alternatively, the substances can be introduced in a matrix. The antibiotics can moreover be physically adsorbed on the surface or—mediated via charged molecules (such as tridodecylmethylammoniumchloride)—bind ionically to the surface. The incremental delivery of these molecules to the surrounding area may be expedient (TYRX™ antibacterial envelope from MEDTRONIC). The use of silver salts, silver ions, and metallic silver is also under discussion.

Additionally, it is known that polymers can be used as surface coatings which replicate the body's own antibiotically acting substances (End-Functionalized ROMP Polymers for Biomedical Applications. Madkour A E, Koch A H, Lienkamp K, Tew G N., Macromolecules. 2010 May 25; 43(10):4557-4561.). Approaches have also been described that are intended to prevent (proteins and) bacteria from adhering by modifying the hydrophobic surface properties, for example by binding hydrophilic chains and polymers (Staphylococcus aureus adhesion to titanium oxide surfaces coated with non-functionalized and peptide-functionalized poly(l-lysine)-grafted-poly(ethylene glycol) copolymers, OHarris L G, Tosatti S, Wieland M, Textor M, Richards R G., Biomaterials. 2004 August; 25(18):4135-48.). This paper also discusses the attempt to combine antibacterial and antiadhesive properties in vitro by using a coating made of polylysine (antibacterial) and polyethylene glycol (preventing the adhesion of biomolecules).

In many of these approaches it is unknown whether these are able to suppress the adhesion of microbes in a long-term stable manner—naturally, degrading processes in the body, which corrode the implant immediately after it has been introduced into the body, decisively influence the surface modification. The surface modification may thus lose the antibiotic action thereof very quickly, as a result of which a biofilm may form on the surface at an explosive rate.

If, additionally, the antibacterially acting substances intervene in the metabolism of the bacteria, minor genetic changes may render the antibiotically acting substances ineffective. The best example is multiresistant bacteria, against which no commercially available antibiotics are effective any longer. Approaches must be found that universally suppress the formation of biofilms, even in multiresistant strains. If antibiotically acting ("drug-eluting") substances are delivered, it is at times possible to cover only short time periods due to the limited amount of the active ingredient.

SUMMARY OF THE INVENTION

The invention provides a method for coating a medical implant which reduces, or else completely suppresses, non-specific adhesion of proteins and/or bacteria and consequently allows a long-term use of implants that is low-risk for a patient. The invention further provides an implant available that evokes few to no defense responses in the patient's body, and can thus be used to treat pathological or undesirable disorders of a patient without risk, the implant optionally being explantable again.

A preferred method for coating a medical implant that includes a membrane having at least pores sized in the nanometer range includes steps of stabilizing the pores with at least one stabilizer; and applying at least one coating by plasma polymerization in the presence of a coating gas and oxygen onto at least one surface of the implant and onto the membrane.

A preferred implant includes a membrane having pores sized in the nanometer range, a surface, and a plasma polymer coating. The surface is at least partially coated with the plasma polymer coating, while the interior of the pores is uncoated

BRIEF DESCRIPTION OF THE DRAWINGS

The invention will be described in more detail hereafter by way of example based on exemplary embodiments illustrated in the drawings. In the drawings.

DETAILED DESCRIPTION OF THE PREFERRED EMBODIMENTS

Figure 1:
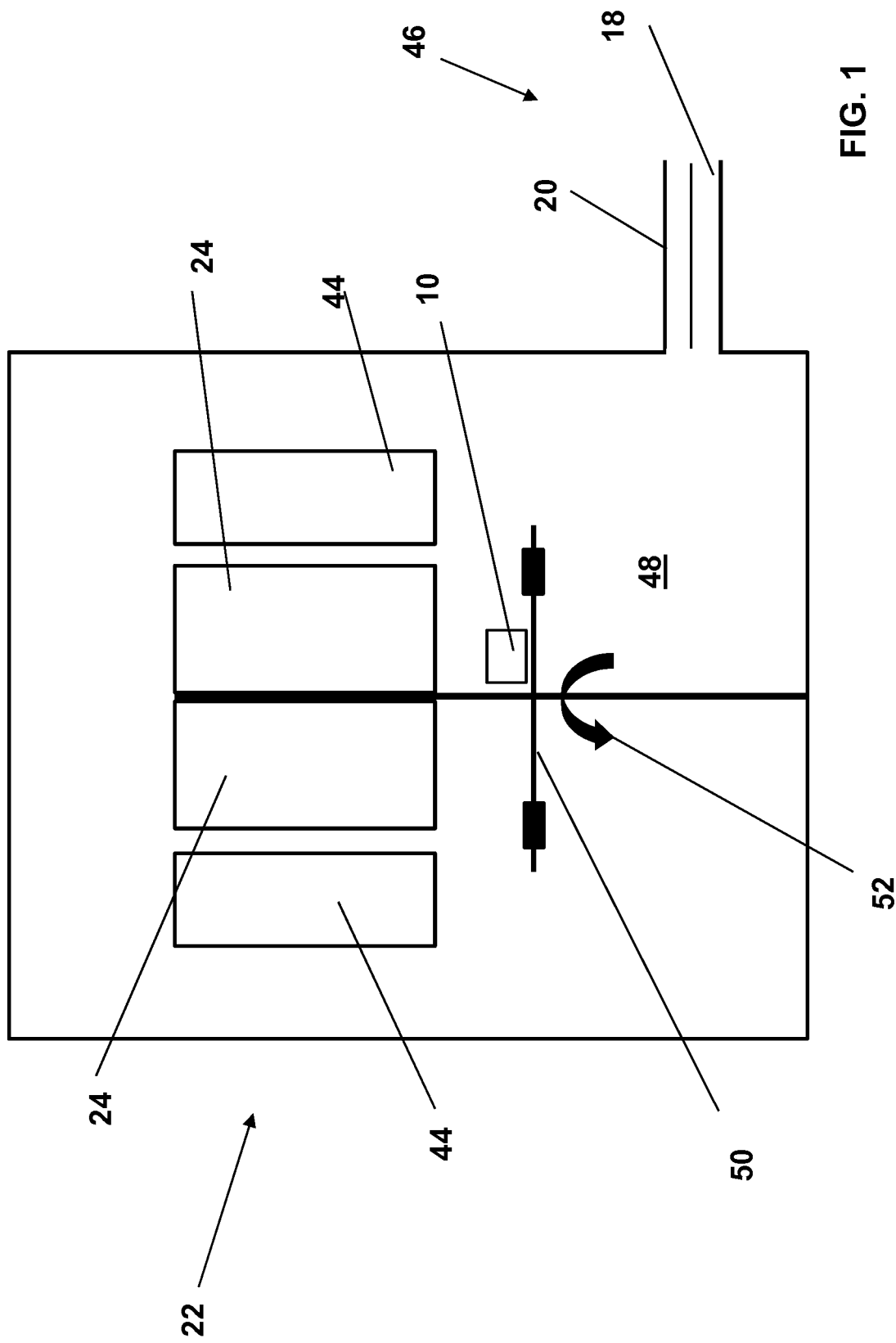
FIG. 1 shows a schematic view of a magnetic field-enhanced plasma polymer system in the low-pressure range.

The invention relates to a method for coating a medical implant that is provided for implantation in an animal body and/or a human body, wherein at least one coating is applied to at least one surface of the implant by way of plasma polymerization.

It is proposed to select at least one coating parameter so that a rough surface of the implant is coated. The design according to the invention makes it possible to coat nanostructured/microstructured implants or substrates. Moreover, by coating surfaces having a certain degree of roughness/porosity, preferably permeability, the adhesion of the coating can advantageously be improved. The more pronounced the adhesion is, the greater is the mechanical stability of the surface against abrasion along the implant surface (or, in general terms, mechanical stress). This improves the suitability of the implant for long-term uses in the body compared to coatings from the related art.

The method is used to generate a mechanically, chemically and biologically stable coating, which is deposited in the form of a plasma polymer and represents a biocompatible interface, wherein the properties of the surface and of the functional areas located beneath, for example having permeability, remain intact. The coating is a surface modification for implants to reduce the implantation risk. The specifically selected physicochemical properties of the coating, and thus of the implant surface, reduce the adsorption of biomolecules and/or cells. This prevents interactions with interfering substances, such as constituent components of structures, such as tissue and/or body fluids, which may come in contact with the implant, and more particularly cells and/or molecular components, such as proteins, salts, ions and/or any other interfering substance deemed harmful by a person skilled in the art. Moreover, the biomolecules adhering in extremely low numbers to the surface are present in a native conformation, whereby the surface (coating) presented to the body is not identified as being foreign at any time. There is natural "camouflaging" of the material with the body's own components. As a result, the surface is advantageously not sheathed/encapsulated in the body's own tissue. Moreover, the surface is likewise not thrombogenic. This coating is long-term stable even in a biological environment. In particular, implants coated by way of a method described herein are particularly suited for implantation, preferably for long-term implantation, since the coating prevents or minimizes ingrowth into the organism, whereby complication-free, or at least complication-minimized, explantation is made possible. This represents a significant advantage with respect to a replacement of the implant compared to implants that were coated according to a method from the prior art. Due to the method proposed herein, it is furthermore possible to provide implants that are not biocompatible with a biocompatible coating and prepare a later explantation by way of the proposed coating.

In this connection, a "rough surface" shall be understood to mean a surface having a surface structure that includes irregularities and/or cavities that have at least the same dimension as structures or particles that can adsorb onto the corresponding surface or pass through the same. The rough surface, however, thus has at least a nano or micro surface roughness and/or a porous structure. The surface has a mean roughness Ra (according to DIN standard 4760) of greater than 0.0008 micrometers (μm). In the range of a nano roughness, the mean roughness Ra ranges between 0.0008 micrometers (μm) and 0.5 μm, for example, and in the range of a micro roughness, the mean roughness Ra ranges between 0.5 micrometers (μm) and 50 μm, for example.

A porous surface shall be understood to mean a surface that comprises one pore, or a plurality of pores, which is or are adapted to a dimension of the structure/substance (such as an analyte or an active ingredient molecule) that is to pass through the porous surface or the pore(s). If the structures are in the nanometer range, the pores can have a maximum diameter of 500 nm, preferably a maximum of 100 nm, more preferably a maximum of 50 nm, advantageously a maximum of 10 nm, and particularly preferably a maximum of 0.5 nm. In larger structures, in contrast, a pore diameter in the micrometer range, and more particularly of up to 50 μm, preferably a maximum of 10 μm, more preferably a maximum of 1 μm, and advantageously a maximum of 800 nm is conceivable.

A coating parameter here represents any parameter of a plasma polymerization system, preferably a magnetic field-enhanced plasma polymerization system, deemed settable or variable by a person skilled in the art considers. These would be, for example, pressure, composition of the coating gas, flow rates (rate of fluid flow) of the coating gas or of the different components thereof, current intensity or output of the plasma polymerization system, frequency and curve progression (pulsed, periodic) of the electrical field of the plasma polymerization system, rotational speed or angular position of a sample holder of the plasma polymerization system, material of the electrodes, presence of further materials influencing the plasma process, process duration, and the like. Advantageously, a plurality of coating parameters are specifically selected.

An implant here represents an aid that is introduced permanently, or at least for an extended time period, into an animal body and/or a human body, in particular invasively, to fulfill a replacement function (long-term implant). The replacement function is to be assumed over multiple days or weeks, and preferably over multiple years or decades. The implant can be any implant deemed appropriate by a person skilled in the art and may be inserted intravenously, intraarterially, subcutaneously, intracardially and epicardially, intravascularly and extravascularly, for example. The implant is in particular selected from the group consisting of: a biosensor, a dialysis device, a drug delivery system, an electrode, a vascular sleeve, a pacemaker, a cardiac pacemaker, a defibrillator, a cardioverter, a brain pacemaker, a neuroprosthesis, electrodes/electronics for artificial extremities, a neurostimulator, a barostimulator, a kidney pacemaker, a duodenal pacemaker, a cardiac implant, a tumor monitoring implant, an artificial heart, an artificial heart valve, a shunt, a brain shunt, a hydrocephalus implant, a telemetry unit, a receiver, a transmitter, a pressure sensor, an organ substitute, an energy harvesting implant, a bio fuel cell, a catheter, a cochlear implant, a retinal implant, a dental implant, an artificial implantable lens system, an implant for joint replacement, a vascular prosthesis or a stent. The method proposed herein may furthermore be used to coat contact lenses and bone implants, such as nails or screws. Preferred fields of use include, for example, cardiac rhythmic management (CRM) devices (cardiac pacemakers/defibrillators), implants for cardiac resynchronization therapy (CRT), leadless pacers/defibrillators, as well as implantable sensors (biosensors, pressure sensors), and drug delivery systems. The implant can in particular also comprise electrical components since it has been shown that these can also be coated by way of the coating protocols according to the invention without loss of unction.

In a preferred embodiment, the implant is selected from the group comprising or consisting of a drug delivery system, a cardiac pacemaker, a defibrillator, a biosensor, an electrode, an artificial heart valve, a pacemaker, a receiver, and a transmitter, or parts thereof.

In a further preferred embodiment, the implant is selected from the group comprising or consisting of a biosensor, a dialysis device, a drug delivery system, a tumor monitoring implant, a telemetry unit, a receiver, a transmitter, and a pressure sensor.

In a further preferred embodiment, the implant is selected from the group comprising or consisting of a biosensor and a dialysis device.

Accordingly, the invention is furthermore based on an implant coated by way of a method according to the invention proposed herein, wherein the implant is selected from one of the above-mentioned groups of possible implants.

An implant thus coated evokes few to no defense responses in the patient's body and can thus be used to treat pathological or undesirable disorders without risk. Moreover, the risks of encapsulation and/or of a bacterial infection are minimized, whereby, in the event of a loss of function, such an implant can also be replaced in a way that is gentle on the patient. It was therefore found that implants, which were coated according to a method proposed herein, can advantageously be explanted since growth of biological material on the implant is prevented, or minimized to such an extent that explantation is possible without complications.

The invention is further based on a method for treating a medical implant that is provided for implantation in an animal body and/or a human body, wherein at least one coating is applied to at least one surface of the implant by way of plasma polymerization.

It is proposed to select a coating parameter so that a surface of the implant having permeability is coated. In this way, a structure can be protected from interfering effects, which is particularly susceptible when it comes to non-specific aggregations and a potentially following encapsulation. Advantageously, the main function of the surface having permeability, which is to say the permeability to substances, and more particularly the selective permeability to certain substances, is preserved. This is relevant in particular in the case of biosensors comprising membranes or dialysis devices comprising permeable dialysis tubing. Such an implant can advantageously be rendered unsusceptible to disturbances in a simple design manner by way of the coating method proposed herein, and moreover it can be explanted without complications.

A "surface having permeability" here shall be understood to mean a surface that allows a substance to pass. This may be unidirectional or else bidirectional. This function may also differ for different substances passing through (size selection). This surface having permeability is preferably a membrane and, for example, a semipermeable membrane. A membrane here shall be understood to mean in particular a planar, rather two-dimensional structure, the extension of which in the length and/or width is greater, or considerably greater, than a depth of the structure. A curved, up to a semi-circular, membrane shall also be covered by the definition of a planar, rather two-dimensional structure. The essential aspect here is that a continuous extension, such as the length or width, is considerably longer (at least five times longer) than a material depth of the membrane. The (material) depth here does not refer to a diameter of the semi-circular shape of the membrane. The pores defining the permeability here are preferably unidirectionally extending formations, in particular substantially perpendicularly to the main extension of the structure or in the direction of the depth. Substantially perpendicular here shall be understood to mean that a deviation of 10% from the strict perpendicular arrangement shall be understood as being perpendicular. The membrane in particular does not include any complex channel structure, as would be the case with a three-dimensional hydrogel, for example.

If implantable biosensors and dialysis devices are used, these membranes have pores on a nanometer scale (dependent on the size of substance, see above). The goal here is that the membrane pores remain freely passable to the analyte or the molecules migrating during dialysis, and are not closed by what is known as fouling, when in contact with body fluids and tissue.

The membrane can be made of any material deemed appropriate by a person skilled in the art, such as polysulfone, polyarylethersulfone (PAES), polyethersulfone (PES), cellulose ester (cellulose acetate, cellulose triacetate, cellulose nitrate), nanocellulose, regenerated cellulose (RC), silicone, polyamide (nylon), polyimide, polyamide imide, polyamide urea, polycarbonate, ceramic, titanium oxide, aluminum oxide, silicon, zeolite (alumosilicate), polyarylonitrile (PAN), polyethylene (PE), polypropylene (PP), polytetrafluoroethylene (PTFE), polyvinylidene fluoride (PVDF), polyvinylchloride (PVC), polypiperazine amide, polyethylene terephthalate (PET), polycarbonate (PC), and the complexes and mixtures thereof.

The membrane is preferably an organic membrane. In this connection, the term "organic membrane" shall be understood to mean a separating layer and/or a thin film, which includes at least one carbon compound-based component. The organic membrane preferably comprises a polymeric substance and/or is formed by a polymeric substance, wherein this substance can be chemically produced so that a pore size of the pores of the membrane is adapted to the molecules used and the measuring principle. The membrane is preferably a polymer membrane made of polyethersulfone.

As described above, the membrane or the polymer membrane comprises at least pores in the nanometer range. To prevent these membrane pores from collapsing in air, the pores are stabilized with at least one stabilizer. This stabilizer may be formed by any substance and/or organic compound deemed appropriate by a person skilled in the art, such as glycerol, glycerol stearates, glycerol esters, other alcohols, salts, or also carbohydrates, for example. The pores are preferably stabilized with glycerol, glycerol stearates or glycerol esters, whereby a sufficiently characterized substance is used. Stabilizing the pores with the stabilizer is preferably carried out by introducing the stabilizer into the pores. The coating parameter, or the coating parameters, must be selected such here that the stabilizer, such as the glycerol, is preserved in the pores and the membrane pores do not collapse. 100% glycerol, or else glycerol diluted with deionized water, may be used as the stabilizer for this purpose. The stabilization further serves to support a site-directed coating of the membrane. During the coating process proposed herein, the stabilizer remains in the pores and not only prevents the membrane from collapsing, and thus clogging, but coating of the interior of the pores in the plasma is also prevented. Thus, it becomes possible for an implant having permeability to be provided with a biocompatible, bioinert and antibiotic coating on the surface, whereby explanting can be implemented without complications, and moreover no loss of function for separation properties of the permeability region is suffered.

Accordingly, it is proposed in a further method step to selectively remove the stabilizer from the surface of the membrane. It is further proposed to carry out the step of selective removal without the supply of gas and using the following parameters: pressure 0.1 to 0.5 Pa, duration: 1 min to 20 min, preferably 1.5 to 15 minutes, and most preferably 8 to 13 minutes. Using the above parameters, it is possible to selectively remove the stabilizer introduced onto and into the membrane from the surface of the membrane, and more particularly from the outer surface of the membrane. Selective removal provides for the stabilizer to remain in the pores, while the stabilizer on the membrane is removed.

As mentioned above, an interesting field of use would be that of coating a biosensor, which comprises at least one medical sensor system, for example. A biosensor here shall be understood to mean a sensor that is used to qualitatively and quantitatively ascertain one or more medically relevant parameters. Furthermore, a sensor system shall be understood to mean a system comprising at least one sensor and/or a specific configuration or arrangement of measuring or ascertaining components—this being a detection system—of the biosensor. This sensor is described in more detail hereafter by way of example. Such an implant can be used in particular to better monitor and treat diseases, such as cardiac insufficiency, high blood pressure, renal insufficiency and/or diabetes mellitus, which are frequent, treatment-intensive and consequently expensive chronic diseases. The described modification of the surface, for example of the membrane, is suited particularly well for an implant since many of the implant surfaces come in contact with body fluid on a regular basis, in particular blood, where defined ingrowth, or precisely no ingrowth, is of particularly high significance.

Implant surfaces susceptible to adsorption include, for example, those made of metal, metal alloys and/or transition metals, compound materials, and resorbable materials. For example, surfaces made of titanium, medical stainless steel, such as preferably 316L, CoCr, gold, magnesium and polymers, are conceivable for this purpose. Polymers may be either degradable in the body under usage conditions or remain permanently in the body. Furthermore, the sensor system may comprise further components, such as additional sensors, a housing, electronic components, a power supply unit, a telemetry unit, a control unit comprising evaluation electronics, an anchoring element and/or any other component that appears appropriate to a person skilled in the art.

Proteins represent a class of substances that are of medical interest. These are involved in many important processes in the blood in the body, for example as enzymes, transport means for other molecules, or as clotting factors. It is of great interest, in particular when a disease is present, to detect such proteins, or the quantity or concentration of the same, in the blood, for example. For this purpose, diagnostics employs, for example, chemical, enzymatic, biochemical, molecular biological, biotechnological, microbiological, nanotechnological, radioactive, physical or optical methods. Proteins have a three-dimensional structure that is defined by the amino acid sequence of the same and that is used by the immune system employing specific antibody recognition, wherein antibodies are able to distinguish foreign from native proteins. This interaction between the antibody and what is known as the antigen can be used for immunological detection and has become established as a common method in in vitro diagnostics. This principle is also used in what is known as a competitive displacement assay ("competition assay") to determine a concentration of the antigen. Furthermore, in vitro methods using no optically measurable markings for molecule detection are known. For this purpose, field effect transistors (FETs) are used in vitro, for example.

In recent decades, it has been shown that an in vitro determination of analytes is often not sufficient to reliably ascertain a current and up-to-date state of the analyte and a condition of a patient associated therewith. Rapid intervention is needed in particular with acute changes, for example in chronically ill patients. In particular, continuous monitoring of analytes and of the concentrations of the same over months, or even years, is advisable. Accordingly, a need exists for a sensor system that is able to reliably and quickly monitor analytes, for example, in vivo over an extended period. It is particularly important in this regard that the functionality is preserved for the longest time possible, which can be ensured by the coating applied according to the invention.

Using such a biosensor, it is possible to ascertain numerous parameters, such as a pH value, an osmolality, a charge, such as of an ion, a polyelectrolyte or a protein, a temperature, a configuration, such as of a binding site, a size, a mass, a state of matter, the water content, the hematocrit level, the partial thromboplastin time, the plasma thrombin clotting time, the Quick's value, a presence or an absence and/or a quantity of a substance and/or of an analyte and/or any other parameter that is deemed useful by a person skilled in the art.

In the majority of cases, however, a specific analyte is measured, such as an electrolyte, a fat, a salt, an ion, a polyelectrolyte, a carbohydrate, a fatty acid, a lipid, a sugar, a nucleotide, a deoxyribonucleic acid, a ribonucleic acid, an amino acid, a peptide, a protein, an antibody, a hormone, a neurotransmitter, a metabolite, a metabolic product, an antigen, an active ingredient, a drug, a nanoparticle, a toxin, water and/or any other substance that is deemed expedient by a person skilled in the art. It is also possible to ascertain a certain state of a molecule, or what is known as a biomarker, which form a variable component of the human or animal body, such as albumins/globulins, alkaline phosphatase, alpha-1-globulin, alpha-2-globulin, alpha-1-antitrypsin, alpha-1-fetoprotein, alpha-amylase, alpha-hydroxybutyrate-dehydrogenase, ammonia, antithrombin III, bicarbonate, bilirubin, carbohydrate antigen 19-9, carcinoembryonic antigen, chloride, cholesterol, cholinesterase, chylomicron remnants, cobalamin/Vitamin B12, coeruloplasmin, C-reactive proteins, cystatin C, d-dimers, iron, erythropoetin, erythrocytes, ferritin, fetuin A, fibrinogen, folic acid/Vitamin B9, free tetraiodothyronine (fT4), free triiodothyronine (fT3), gamma-glutamyltransferase, glucose, glutamate dehydrogenase, glutamate oxalacetate transaminase, glutamate pyruvate transaminase, glycohemoglobin, packed cell volume, hemoglobin, haptoglobin, uric acid, urea, HDL cholesterol, homocysteine, immunoglobulin A, immunoglobulin E, immunoglobulin G, immunoglobulin M, INR, potassium, calcium, creatinine, creatine kinase, copper, lactate, lactate dehydrogenase, LDL cholesterol, leukocytes, lipase, lipoprotein, magnesium, corpuscular hemoglobins, myoglobin, sodium, NT-proBNP/BNP, phosphate, prostate-specific antigens, reticulocytes, rheumatoid factor, thrombocytes, thyreoidea stimulating hormone, transferrin, triglycerides, troponin T, and VLDL cholesterol.

An analyte shall also be understood to mean an "active ingredient," wherein the term "active ingredient" comprises typical pharmaceuticals, or else metabolites, which are administered for treating diseases, such as muscarinic receptor antagonists, neuromuscular blocking agents, cholesterol esterase inhibitors, adrenoceptor agonists, indirectly acting sympathomimetic drugs, methylxanthine, alpha-adrenoreceptor antagonists, ergot alkaloids, beta-adrenoceptor antagonists, inactivator inhibitors, antisympathonic drugs, 5-HT receptor agonists, histamine receptor agonists, histamine receptor antagonists, analgesics, local anesthetics, sedatives, anticonvulsant drugs, convulsant drugs, muscle relaxers, anti-Parkinson's drugs, neuroleptics, antidepressants, lithium, tranquillizers, immunosuppressants, antirheumatism drugs, antiarrhythmic drugs, antibiotics, ACE inhibitors, aldosterone receptor antagonists, diuretics, vasodilators, positive inotropic agents, antithrombotic/thrombolytic substances, laxatives, antidiarrheal drugs, pharmaceuticals for adiposity, uricostatic drugs, uricosuric drugs, lipid lowering drugs, antidiabetics, antihypoglycemic drugs, hormones, iodized salts, threostatic drugs, iron, vitamins, trace elements, virostatics, antimycotics, antitubercular drugs, and substances for tumor chemotherapy. The feature to be analyzed preferably relates to a variable component of the animal and/or human body. Many of these analytes can be determined in a body fluid, such as lymph fluid, saliva, urine, gastric juice, secretions of the pancreas, bile, sudor, lacrimal fluid and the interstitial fluid, extracellular fluid, breast milk, female vaginal secretion, lacrimal fluid, nasal discharge, ejaculate, menstrual fluid, aqueous humor of the eye, cerebrospinal fluid, ascites, pleural fluid, pericardial fluid, synovial fluid, amniotic fluid, cerumen, pus, liquor and/or in particular blood, to characterize the state of health of individuals, in particular in the case of chronic diseases, such as cardiac insufficiency, or renal insufficiency. The sensor system could be used, for example, to detect a member of the cystatin family of the cysteine protease inhibitors or to detect cystatin C, and would thus be a cystatin C sensor.

A sensor shall in particular be understood to mean a component that is able to qualitatively and/or quantitatively detect an optical, physical, chemical, biochemical, molecular biological, nanotechnological, radioactive, enzymatic and/or electrochemical property of the feature in an environment of the sensor, for example in the form of a measured variable. The detection system integrated into the sensor is specifically tailored to the parameter to be ascertained/measured, or the desired property, for this purpose.

Such a sensor can comprise at least one semiconductor component, for example. A semiconductor component here shall be understood to mean a FET-based (field effect transistor-based) active component, such as an seFET (extended gate field effect transistor), an ISFET (ion-sensitive field effect transistor), an EPROM (electrically erasable programmable read-only memory) or an EEPROM (electrically erasable programmable read-only memory), a capacitor, a nanotube, a nanowire and/or any other semiconductor component deemed appropriate by a person skilled in the art. As an alternative, an impedimetric, amperometric, potentiometric, conductometric or capacitive system may be used as the sensor. This design allows the sensor system to be implemented particularly easily in a miniaturized format.

As mentioned above, the implant can comprise a membrane, and more particularly an organic membrane, in the coated surface. At least one reservoir of the sensor can be closed off by way of this membrane. The term "closed off" here shall not mean that a transport of substances between the reservoir and an external region is entirely prevented; it merely means that a space is defined, in which certain components of the sensor system are disposed and/or retained. A "reservoir of a sensor" or a "sensor reservoir" here shall be understood to mean a space, a chamber and/or a cavity of the sensor, which the detection system of the sensor is in contact with and/or on, and preferably in, which the detection system or the competition assay is disposed. A bottom of the reservoir, located opposite the semipermeable membrane, preferably has what is known as a "gate" of a semiconductor component or of an seFET. The sensor reservoir furthermore encloses at least one volume, and more particularly a sample volume, which can include or contain the feature that is to be detected. The organic membrane can advantageously be used to establish which molecules can come in contact with the sensor, and which cannot. This again demonstrates how crucial it is that the functionality of the membrane in the body is preserved.

With respect to the methods proposed herein, it is particularly advantageous for the coating of implants if the coating process by way of plasma polymerization is carried out in the presence of oxygen. In a further preferred embodiment of the methods proposed herein, it is particularly advantageous for the coating of implants if the coating process by way of plasma polymerization is carried out in the presence of at least one saturated hydrocarbon, which is preferably selected from the group comprising or consisting of saturated C1 to C6 hydrocarbons, and more preferably selected from the group comprising or consisting of methane, ethane, propane and butane. In a particularly preferred embodiment, the coating process is carried out in the presence of methane. Hydrocarbons here shall be understood to mean traditional compounds composed of carbon and hydrogen, which moreover comprise only single bonds when in the "saturated" form.

It has been shown that an adhesion of interfering substances can be prevented particularly efficiently if the surface is coated using the following coating parameters: pressure: 1 pascal (Pa) to 10 Pa, flow rate of a coating gas: 0 standard cubic centimeters per minute (sccm) to 10 sccm, current intensity of the plasma polymerization system: 100 milliamperes (mA) to 500 mA, rotational speed of the sample holder: 0 revolutions per minute (rpm) to 5 rpm, coating time: 1 minute (min) to 200 min, preferably 20 min to 100 min, and particularly preferably 60 min, electrode of the plasma polymerization system: titanium, titanium content: between 50% and 100% titanium. The flow rate can also be referred to as the rate of fluid flow and is indicated in ml/min. It shall be noted that the rotational speed of the sample holder becomes negligible at coating times of greater than 5 minutes.

In a preferred embodiment, a coating is applied according to a method proposed herein using the following coating parameters: 1 pascal (Pa) to 10 Pa, flow rate of oxygen and at least one saturated hydrocarbon: 0 standard cubic centimeters per minute (sccm) to 10 sccm, current intensity of the plasma polymerization system: 100 milliamperes (mA) to 500 mA.

In a preferred implementation, the at least one coating parameter is selected so that an oxygen-containing hydrocarbon coating or layer is formed. This can be achieved in particular when the coating process is carried out in the presence of oxygen and at least one saturated hydrocarbon, which is preferably selected from the group comprising or consisting of methane, ethane, propane and butane, and more preferably methane. The high hydrophilicity and the further advantageous physical and chemical properties of such layers make these particularly suitable for "camouflaging" the implant surface. The few adhering proteins remain in the native structure thereof, whereby the body does not identify these implant surfaces as being foreign at any time. Ingrowth of an implant that is coated according to the invention is thus in particular made more difficult or prevented.

It has been shown that a coating using the following coating parameters is advantageous for an implant: pressure: 5 Pa, flow rate of the methane coating gas: 2.5 sccm, flow rate of the oxygen coating gas: 1.3 sccm, current intensity of the plasma polymerization system: 200 mA, electrode of the plasma polymerization system: 100% titanium. A rotational speed of the sample holder is preferably 2 rpm. A coating time is advantageously 1 min to 200 min, preferably 20 min to 100 min, and particularly preferably 60 min. Potential pretreatments, such as special cleaning steps (hydrofluoric acid bath, for example) or the application of an adhesion promoter layer (see below), are not absolutely necessary. An implant thus coated essentially exhibits an inconspicuous behavior of the implant surface in the body, which is particularly important in an implant that can be introduced into a bloodstream of an animal body and/or a human body, since a life-threatening formation of thrombi is possible here.

As described above, when coating a membrane, and more particularly a polymer membrane, in particular the presence of the stabilizer (preferably glycerol) is critical, or the integrity of the same during the coating process is decisive for ensuring that the biosensor continues to operate reliably. The coating parameters are selected so that the glycerol on the surface of the membrane evaporates, and the glycerol in the pores is preserved, prior to applying the plasma polymer layer. In this way, the surface of the membrane may be coated with plasma polymers, while the stabilizer remains preserved in the pores. This was successfully achieved by optimizing the method parameters, in which the glycerol on the surface of the membrane is removed, not however in the pores. This approach takes advantage of the fact that the vapor pressure of glycerol is in the pressure range that prevails or is set during the coating process in the plasma polymerization system. When the vacuum is generated by the butterfly valve to the vacuum pump being opened, the optimized vacuum cycle can be influenced, for example by way of the pumping capacity, whereby the glycerol begins to evaporate due to the vapor pressure. This can be monitored based on the progression of the pressure curve. In general, it can be observed that the time period until the desired final pressure is reached is longer in the presence of glycerol, compared to test conditions without glycerol.

It has been shown that it is particularly advantageous when a membrane, and more particularly a polymer membrane, of an implant is coated using the following coating parameters, wherein the membrane, and more particularly the polymer membrane, comprises pores in the nanometer range: pressure: 1 Pa to 3 Pa, flow rate of the methane coating gas: 2.5 sccm, flow rate of the oxygen coating gas: 1.3 sccm, current intensity of the plasma polymerization system: 375 mA, electrode of the plasma polymerization system: 100% titanium. A rotational speed of the sample holder is preferably 2 rpm. A coating time is advantageously 1 min to 200 min, preferably 20 min to 100 min, and particularly preferably 60 min. Potential pretreatments, such as special cleaning steps (hydrofluoric acid bath, for example) or the application of an adhesion promoter layer (see below), are not absolutely necessary.

According to a further embodiment of the invention, the at least one coating parameter is selected so that a layer thickness of the coating of 1 nanometer (nm) to 200 nm, preferably of 2 nm to 100 nm, and particularly preferably of 15 nm to 50 nm is obtained. These layer thicknesses have proven particularly useful in experiments. A good balance between stable adhesion of the plasma polymer layer and reduced protein adsorption was found in particular in the medium layer range (15 nm to 50 nm). Moreover, thinner layers result in the advantage that shorter coating times suffice to obtain an adequate layer thickness. A layer thickness of approximately 25 nm was found to be particularly advantageous.

The present invention thus also relates to implants comprising a membrane that includes at least pores, preferably in the nanometer range, a surface, and a coating, wherein the coating is applied by way of plasma polymerization, and wherein the surface is at least partially coated, and wherein the interior of the pores is uncoated. The present invention further also relates to implants comprising a surface having permeability and a coating, wherein the coating comprises the elements carbon, nitrogen, oxygen and a metal, which is selected from the group comprising or consisting of titanium, silver, copper, zinc, mercury, tin, lead, bismuth, cadmium, chromium, and thallium, and the alloys thereof. In a preferred embodiment, the surface having permeability represents a membrane as proposed herein, comprising pores as described herein. An implant as proposed herein comprises a coating only on the surface, but not in the interior of the pores. In a preferred embodiment, the metal is titanium or a titanium alloy. In a further preferred embodiment, the coating has a layer thickness of 1 nanometer (nm) to 200 nm, preferably of 2 nm to 100 nm, and particularly preferably of 15 nm to 50 nm. In a further preferred embodiment, the implants proposed herein comprise coatings that are free from aldehyde groups.

A surprising effect that was furthermore found was that sensitive electrical components, such as those of a cardiac pacemaker, are not damaged by the coating conditions. The possibility of applying the plasma polymer coatings onto electrical components significantly increases the compatibility of implants with such components. If care is taken that the plasma polymer coatings do not have insulator properties at these layer thicknesses, it is also possible to apply plasma polymer coatings to electrodes (such as stimulation electrodes) or sensor electrodes. In this regard, in particular the layer thickness is the decisive factor. Thin layer thicknesses between 3 nm and 100 nm have negligible insulator properties. The selection of the output of the plasma polymer system has little influence on the formation of insulator properties. It has been shown that both encapsulation of the electrodes and a bacterial infection are prevented, while dielectric properties of the electrode remain substantially unimpaired.

As indicated above, it would be possible to subject the surface of the implant to a pretreatment prior to the plasma polymer coating process. For this purpose, any pretreatment deemed appropriate by a person skilled in the art would be conceivable, such as a special cleaning step (referred to as a hydrofluoric acid dip), an application of a primer by way of spraying, immersion, brushing, and the like.

The application of a plasma polymer layer having the above-described positive properties is only possible with difficulty, or insufficiently successful, on certain substrates. An increased range of materials can only be covered by improving adhesion properties. A particularly advantageous pretreatment, however, is the application of an adhesion promoter layer. By coating the substrates with adhesion-promoting layers (referred to as layer stacks), the plasma polymers can be applied to any conceivable substrate. Moreover, the use of adhesion-promoting layers allows the spectrum of coatable materials to be broadened by matching the surface energies of the individual layers in the layer stack to each other. Moreover, this yields a general improvement in the adhesion of the plasma polymer layers to the implant surface. To accomplish this, all that is needed is to adapt the coating by way of plasma polymerization to the material properties of the adhesion promoter layer. In this way, a universal coating protocol is obtained for all implant surfaces, which is merely dependent on the adhesion promoter layer. By using the layer stack, it is possible to coat any conceivable material with plasma polymers, wherein clever selection of the individual layers allows drastically improved adhesion to be achieved. An adhesion promoter layer here shall be understood to mean a layer that "mediates" an adhesion of the plasma polymer layer to the surface, or is needed to make the same possible in a stable and permanent manner. In principle, these may also be several consecutive—firmly adhering—layers.

In principle, the pretreatment to promote adhesion may also be a non-layer-forming pretreatment. This would be possible by way of plasma treatment using oxygen or argon, for example. A surface energy is likewise matched thereby, which enables coating with a plasma polymer layer.

The adhesion promoter layer is particularly preferably a polymer layer, and more particularly a plasma polymer layer, which is applied by way of plasma polymerization. Using the same technology for the target coating (interface interacting with the body) and the adhesion promoter layer reduces the apparatus-related complexity for generating these layers. An adhesion promoter layer that can be used for numerous implant surfaces and that is also easy to coat by way of plasma polymerization can be obtained when the adhesion promoter layer is applied using the following coating parameters: pressure: 5 Pa, flow rate of the methane coating gas: 2.5 sccm to 5 sccm, flow rate of the oxygen coating gas: 0 sccm to 2 sccm, current intensity of the plasma polymerization system: 200 mA. The electrode material can be any arbitrary conductive material, such as titanium, aluminum, stainless steel, copper, or gold. A rotational speed of the sample holder is preferably 2 rpm. A coating time is advantageously 1 min to 200 min.

The final interface, which is in contact with the biological environment, is applied to the adhesion promoter layer using the following coating parameters: pressure: 5 Pa, flow rate of the methane coating gas: 2.5 sccm, flow rate of the oxygen coating gas: 1.3 sccm, current intensity of the plasma polymerization system: 200 mA, electrode of the plasma polymerization system: 100% titanium. A rotational speed of the sample holder is preferably 2 rpm. A coating time is advantageously 1 min to 200 min, preferably 20 min to 100 min, and particularly preferably 60 min.

To further improve the compatibility of the implant, the coating on the surface of the implant is sterilized. According to an advantageous embodiment, the coating is sterilized by way of ethylene oxide. This represents an important advantage since there is no adverse effect of the ethylene oxide on the plasma polymer layer, and the reduced interaction of the same is also preserved after sterilization. In this way, a health risk of the implant for the body may be further reduced. Sterilization by way of ethylene oxide moreover has the advantage that, after the sterilization, the plasma polymer layer returns quickly to the original state, which is to say a state having a high degree of swelling. This is attributed to the fact that the plasma polymer layer and ethylene oxide have similar chemical compositions.

For some applications it may be useful that biomolecules are not able to adhere. This can be achieved, for example, by masking select reactive chemical groups of the coating. It has been shown that most notably aldehyde groups, serving as reactive chemical groups, are responsible for the interaction activity of the coating with adhering structures. An advantageous aspect is thus to reduce reactive chemical groups of the coating using a reducing reagent. In this way, colonization of the plasma polymer coating may be considerably reduced further. The reduction here is carried out in particular by way of at least one reducing reagent from the group consisting of: sodium borohydride, tris(hydroxymethyl)aminomethane (TRIS), ethanolamine, and glycine. Sodium borohydride proved to be the most effective for this purpose. The approach of subsequently chemically masking chemical groups that may interact with biomolecules helps improve the properties of the surfaces. The treatment is carried out as follows: dissolve 1 mg/ml $NaBH_4$ in 10 mM PBS buffer, incubate the surface to be modified for 1 hour at room temperature, followed by one or more washing steps.

If interfering substances should nonetheless still adsorb in low quantities onto the modified surface, despite modification of the reactive chemical groups, these adhering biomolecules are present in a native three-dimensional structure, whereby the surface (coating) presented to the body is not identified as being foreign at any time. There is natural "camouflaging" of the material with the body's own components. As a result, the surface is advantageously not sheathed/encapsulated in the body's own tissue. Moreover, the surface is likewise not thrombogenic. This coating is long-term stable even in a biological environment.

In principle, it is possible to coat all implant surfaces. However, it would also be conceivable to coat only individual portions or regions of the implant. For this purpose, the resulting coating-free regions could be covered or taped off prior to the coating process. It would also be conceivable to apply an inhibiting substance to prevent the deposition of the plasma polymer layer. It would also be possible to apply a substance to the surface which is dissolved after the plasma polymer layer has been applied, whereby the substance and the plasma polymer layer are removed. Moreover reactive ion etching, wet-chemical etching, laser ablation, or electropolishing would be possible.

The implant can comprise at least one functional sector, for example in the form of an analysis sector or a delivery sector (for releasing substances), and at least one attachment sector or an anchoring component. To take the different functions into consideration, these regions can also be treated differently with respect to the coating of the surfaces of the same. They can be coated using different conditions and thus comprise coatings that differ from each other. Or it would be possible to coat only one of the regions. To ensure the reliable function of the functional sector or analysis sector (preventing the encapsulation at the functional (measuring) part to preserve the measuring function), the same is preferably coated. The attachment sector, in contrast, remains uncoated, whereby the same will be at least partially encapsulated, whereby a desirable improvement in or stabilization of the anchoring of the implant in the tissue may be enabled.

To reduce the risk of infection, it is particularly advantageous if the coating, and thus the implant surface, in addition to the reduced adsorption property, has suitable properties that suppress the initial adhesion of microorganisms, or at least prevent the explosive reproduction and the formation of the biofilm. Accordingly, the at least one coating parameter is selected so that a coating having antibiotic properties is obtained. The antibiotic properties of the coating/of the surface result in fewer complications with implants, or the implantation thereof, or the replacement thereof. In this context, the term antibiotic shall be understood to mean "inhibiting the growth of microorganisms or killing the same."

According to one advantageous implementation, it is provided that at least one antibiotically acting metal is introduced into the coating. This allows the antibiotic action to be preserved over a long period since the antibiotically acting reagent is implemented in one piece with the coating, and thus is inseparable from the same. It is possible for this purpose to carry out the introduction into the coating during or after the coating process. The method proposed herein thus furthermore comprises the step of applying a coating by way of plasma polymerization in the presence of a metal, which is at least partially incorporated into the coating. Any method deemed appropriate by a person skilled in the art would be conceivable to introduce and/or apply the metal or the particles thereof. All—chemical or physical—methods for depositing thin films (thin-film deposition) would be conceivable for this purpose, such as a sol-gel process (dip coating, spraying, spin coating); plating (electroplating, electroless plating); chemical vapor deposition, metal-organic chemical vapor deposition (MOCVD), plasma-enhanced chemical vapor deposition (PECVD), low pressure chemical vapor deposition (LPCVD), thermal vapor deposition (thermal VD), atomic layer deposition (ALD); evaporation, ion plating, laser ablation, molecular beam epitaxy (MBE), electron beam evaporation, thermal evaporation, ion assisted deposition (IAD); sputtering (radio frequency sputtering (RF sputtering), direct current sputtering (DC sputtering), magnetron sputtering, and ion beam sputtering (IBS)).

The introduction is preferably carried out by applying the coating in the presence of at least one antibiotically acting metal. The embedding essentially results on its own by virtue of the coating conditions. It would be possible, for example, to place a small amount of the antibiotically acting metal in the reaction chamber, from which metal ions are knocked out by the excited field during operation of the plasma reactor and embedded in the coating.

As an alternative and/or in addition, it would be possible, and this would be achievable using a particularly simple design, to knock the antibiotically acting metal out of the electrode of the plasma polymerization system during the coating process. Metals selected from the group comprising or consisting of titanium, silver, copper, zinc, mercury, tin, lead, bismuth, cadmium, chromium, and thallium, and the alloys thereof, can be used for the method proposed herein. Suitable metals that could be used further include silver, copper, zinc, mercury, tin, lead, bismuth, cadmium, chromium, and thallium, and the alloys thereof, or preferably titanium and titanium alloys. In a preferred embodiment, titanium or a titanium alloy is introduced into the coating. It was found that the use of titanium or of a titanium alloy results in titanium particles or titanium alloy particles being found in the coating. While titanium or titanium alloys per se are not known to be antibiotic, it was furthermore surprisingly found that these coatings develop an antibiotic action. This antibiotic action also occurs, or remains, without any further irradiation of UV light.

A coating using the following coating parameters has proven to be particularly advantageous for a coating having antibiotic properties: pressure: 1 Pa to 10 Pa, flow rate of the methane coating gas: 1 sccm to 5 sccm, flow rate of the oxygen coating gas: 0.5 sccm to 2 sccm, current intensity of the plasma polymerization system: 100 mA to 300 mA, coating time: 1 minute (min) to 200 min, electrode of the plasma polymerization system: titanium, titanium content: >50%.

Considerably better results were achieved using the following coating parameters: pressure: 4 Pa to 6 Pa, flow rate of the methane coating gas: 2.5 sccm to 3 sccm, flow rate of the oxygen coating gas: 1 sccm to 1.5 sccm, current intensity of the plasma polymerization system: 150 mA to 250 mA, coating time: 10 min to 200 min, electrode of the plasma polymerization system: titanium, titanium content: 100%.

The best results were yielded using the following coating parameters: pressure: 4 Pa to 6 Pa, flow rate of the methane coating gas: 3 sccm, flow rate of the oxygen coating gas: 1 sccm, current intensity of the plasma polymerization system: 150 mA to 250 mA, coating time: 30 min to 200 min, electrode of the plasma polymerization system: titanium, titanium content: 100%. In all three listed protocols, a rotational speed of the sample holder was preferably 2 rpm. It was found, for example, that, by way of the layers thus generated, a layer thickness of approximately 20 nm, and embedded titanium of approximately 1%, allowed an improvement in the antibiotic action compared to control layers of 65% to 99% to be achieved.

A preferred embodiment of the invention is thus the use of the method of magnetic field-enhanced plasma polymerization to generate a biocompatible and antibacterial coating on an implant surface. Or, in other words, a surface coating is to be obtained which not only suppresses the encapsulation of the implants and does not act thrombogenically, but is also antibiotically active.

To amplify the antibiotic action of the plasma polymer layer, it may be additionally advantageous for the method proposed herein to comprise a step in which the coating is treated with UV or near-UV light. This can take place during or after the treatment in the plasma reactor. The UV light, preferably having a wavelength of less than 385 nm, causes photocatalysis. This, in turn, leads to the formation of oxygen radicals, which have a damaging effect on bacteria. The antibiotic action of the plasma polymer layer can in particular be increased when a coating containing an antibiotically acting metal, as proposed herein, is treated with UV light or near-UV light. Due to the presence of the antibiotically acting metals, the formation of oxygen radicals can be drastically increased with UV light or near-UV light.

In the figures, functionally equivalent or equivalently acting elements are denoted by the same reference numerals. The figures are schematic illustrations of the invention. They depict non-specific parameters of the invention. In addition, the figures only reflect typical embodiments of the invention and are not intended to limit the invention to the shown embodiments.

To avoid unnecessary repetitions, elements in a figure that are not described in detail are provided with a reference to the respective description of the elements in the preceding figures.

FIG. 1 shows a schematic view of a magnetic field-enhanced plasma polymerization system 22 for carrying out the method according to the invention. Plasma polymerization is generally understood to mean the formation of a material resulting from an organic gas or gas mixture under the action of an electric discharge. A wide variety of collisions, such as excitation, ionization and recombination of the involved species, take place in the plasma. The plasma polymerization system 22, also referred to as a plasma reactor, comprises two opposing electrodes 24, which are preferably made of titanium. Magnets 44 disposed in a circle are situated on the side of these electrodes 24. The resulting magnetic field focuses the glow discharge between the electrodes 24 and increases conductivity. This is achieved by an increased ion density, electron density, and electron temperature. A so-called "race track" forms on the electrode material with the aid of magnetic field enhancement. This race track is created in a position where the vertical component of the magnetic field is zero, since the magnetic field is perpendicular to the electrical field lines here.

The plasma polymerization system 22 is used to deposit a coating 12, 12', 12", 12''' in the form of a nanofilm onto a substrate, such as a surface 14, 16 of an implant 10 (see below). The deposition is carried out at a pressure of 1 pascal (Pa) to 10 Pa in fine vacuum. A starting substance of the coating 12, 12', 12", 12''' used here is a gas mixture composed of the coating gases methane 18 and oxygen 20. These gases are metered by way of mass flow regulators and conducted via a feed system 46 into a reactor volume 48 of the plasma polymer system 22. A flow rate of the coating gases 18, 20, or the rate of fluid flow, or also the mass flow, is between 0 standard cubic centimeters per minute (sccm) and 10 sccm, and preferably between 0 sccm and 5 sccm. The flow rate can also be indicated in ml/min. A current intensity of the plasma polymerization system 22 is between 100 milliampere (mA0 and 500 mA. In addition, the coating is carried out in the AF range (1000 to 2000 hertz (Hz)). The introduced power of the system is between 20 and 100 watt (W). The samples, or the implant 10 to be coated, are located on a sample holder 50 in the form of a wheel rotating in the rotational direction 52 axially between the electrodes 24 on what is known as a "floating" potential.

As mentioned above, the plasma polymerization system 22 is used to apply a coating 12, 12', 12", 12''' onto a surface 14, 16 of an implant 10. Before going into greater detail of the coating process, first the operating principle of the implant 10 will be described to better illustrate the advantages of the method according to the invention.

Figure 2:
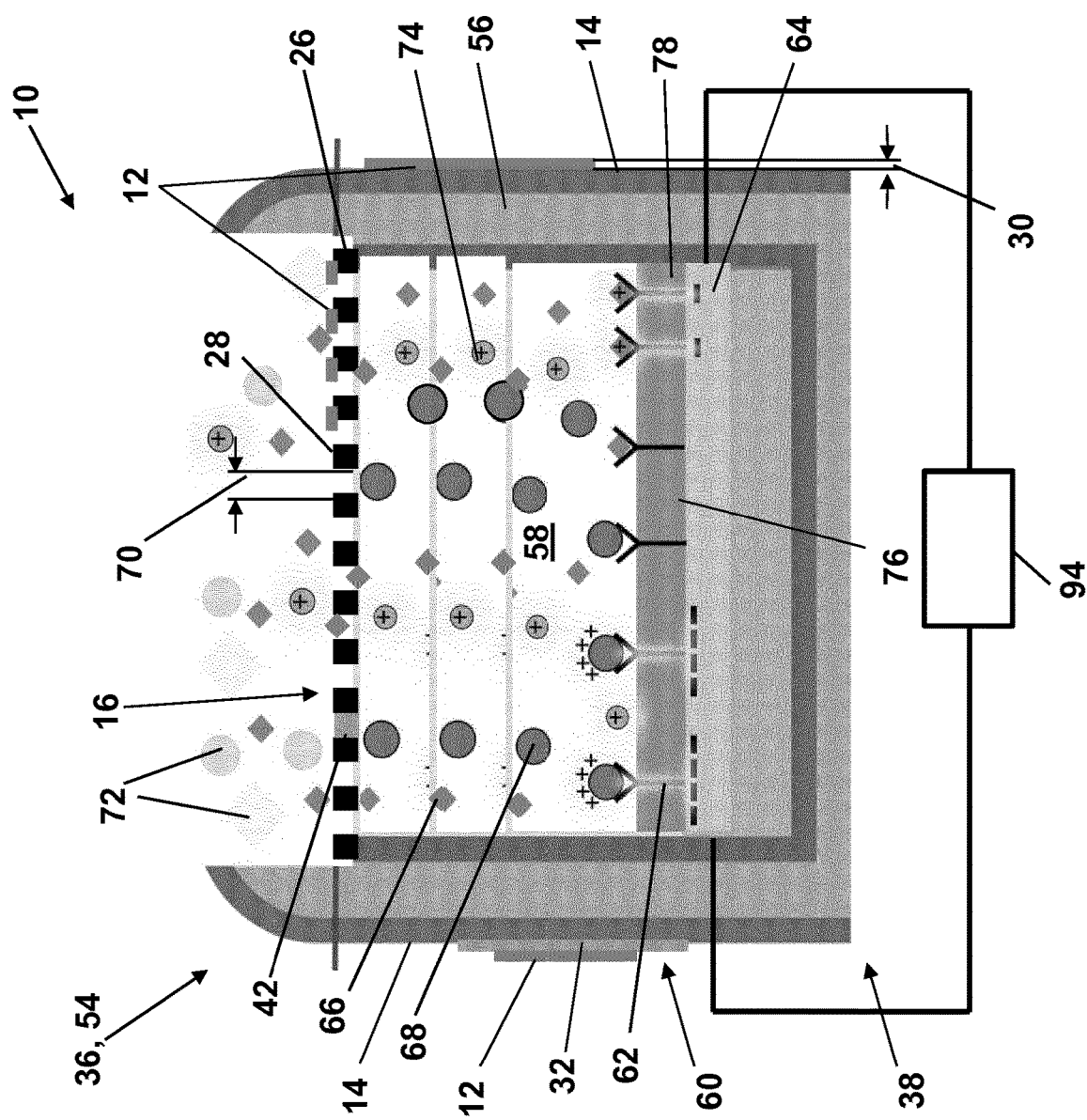
FIG. 2 shows a sectional view through an implant in the form of a biosensor, coated in the plasma polymer system of FIG. 1 with a plasma polymer layer by way of the method according to the invention.

As can be seen in FIG. 2, which shows a sectional view through the implant 10, the implant 10 is designed as a biosensor. This biosensor comprises a sensor system 54 including a reservoir 58, which is substantially closed off or surrounded by a housing 56 and encloses a sample volume. A detection system 60 is disposed in the reservoir 58 or on a lateral surface. The biosensor moreover comprises a selection structure in the form of a membrane 26, and specifically in this embodiment in the form of an organic semipermeable polymer membrane 26 made of polyethersulfone, which according to this exemplary embodiment is disposed on a side of the reservoir 58 located opposite the lateral surface comprising the detection system 60. A polymer membrane 26 made of polysulfone is described hereafter as one embodiment. However, the membrane 26 can also be made of any material deemed appropriate by a person skilled in the art, such as polysulfone, polyarylethersulfone (PAES), polyethersulfone (PES), cellulose ester (cellulose acetate, cellulose triacetate, cellulose nitrate), nanocellulose, regenerated cellulose (RC), silicone, polyamide (nylon), polyamide imide, polyamide urea, polycarbonate, ceramic, titanium oxide, aluminum oxide, silicon, zeolite (alumosilicate), polyarylonitrile (PAN), polyethylene (PE), polypropylene (PP), polytetrafluoroethylene (PTFE), polyvinylidene fluoride (PVDF), polyvinylchloride (PVC), polypiperarinamis, polyethylene terephthalate (PET), polycarbonate (PC), and the complexes and mixtures thereof.

The detection system 60 comprises a plurality of receptors 62, which are used to coat the lateral surface in a density known to a person skilled in the art, serving as the receptor layer. The bottom comprises a semiconductor component 64 in the form of an extended gate field effect transistor (seFET) known from the prior art comprising a gate. The receptor 62 is formed by a molecule, which has an antigen recognition site and is a Fab fragment of a monoclonal antibody against a protein to be detected or an analyte 66 containing the antigen to be recognized.

The analyte 66, which in the present case is cystatin C by way of example, has a feature to be detected by the detection system 60, which is a positive charge here. Depending on the analyte used, the charge may also be negative. In addition, an antagonist 68 of the analyte 66 is present in the reservoir 58, the antagonist likewise carrying the antigen to be recognized by the receptor 62. This antagonist 68 is an artificial and recombinant protein developed with epitope mapping, which carries a poly-L-lysine modification. The antagonist 68 furthermore also carries the feature to be detected, or the positive charge. The antagonist 68 and the receptor 62 are moreover molecular biologically modified so that several amino acids, which are present in the sequences of the same and not important for binding of the respective opponent, however which are recognized as starting points for degradation by internal metabolic enzymes (such as serine of serine proteases), are replaced by other amino acids that do not change the protein structure. This will protect the molecules from enzymatic degradation in the body, whereby the long-term stability is increased (not shown in detail).

The organic polymer membrane 26 is designed so that the antagonist 68 is retained in the reservoir 58 at all times, and that the analyte 66 is able to pass the membrane. For this purpose, the polymer membrane 26 comprises a plurality of pores 28, which are homogeneously distributed over the surface. The pores 28 are not shown true to scale, but are enlarged. A diameter 70 of the pore 28 of the polymer membrane 26 must be larger than approximately 5 nm for the analyte 66, this being cystatin C, to diffuse through. However, it must be smaller than 20 nm, to retain the antagonist 68 in the reservoir 58. Additional cells 72 or molecules 72, or interfering substances 72 in general, which are larger than the pore diameter 70, are retained by the polymer membrane 26. However, micromolecules 74 are able to pass the polymer membrane 26. The polymer membrane 26 and the semiconductor component 64 are connected to the housing 56 so that a mass transfer is possible only via the pores 28 of the polymer membrane 26, and not via a connecting point between the polymer membrane 26 and the housing 56.

If a sensor were to be used to detect or determine glucose or similarly small molecules, for example, a pore diameter of approximately 1 nm would suffice for the glucose to pass the membrane.

As mentioned above, both the analyte 66 and the antagonist 58 carry the feature to be detected or the positive charge. As a result of the poly-L-lysine modification, the antagonist 68 has a large positive charge and a higher charge than the analyte 66. These consequently differ in terms of the charge intensity.

The sensor principle is based on a marking-free immunological detection method, in which the analyte 66 can be measured reversibly and as a function of the concentration. The gate of the seFET comprises the bound receptors 62 selectively recognizing the analyte 66. These are saturated by the antagonist 68 present in the sample volume when the analyte 66 is absent, and in particular also prior to the first measurement. The high charge of the antagonist 68 generates a measurable charge transfer on the sensitive surface of the semiconductor component 64, whereby a measurement signal is generated on the seFET, which can be ascertained by a measuring unit 94. Due to the saturation of the sensor with the antagonist 68, the measurement signal is 100% in the absence of the analyte 66.

If analyte 66 from the measuring substance, which surrounds the sensor and is blood, for example, now enters the sample volume of the sensor via the polymer membrane 26, this analyte may interfere with the existing bond between the antagonist 68 and the receptor 64. If the analyte 66 is present on the active surface, the analyte 66 and the antagonist 68, due to the similar respective antigen of the same, compete substantially equally and with equal intensity for the antigen recognition site of the antibody fragment (Receptor 64). The antigen of the analyte 66 thus causes a reversible displacement of several of the antagonists 68 that have a high charge and are bound to the receptor 64. A concentration-dependent equilibrium develops between bound analyte 66 and bound antagonist 68, wherein the charge transfer for the analyte 66 and the antagonist 68 is different. Overall, the more analyte 66 is bound, the lower is the measurement signal that can be derived.

The sensor ascertains the electrical state variable or a change in voltage. Due to the large difference in charge between the analyte 66 and the antagonist 68, the change in the concentration is clearly detectable. The analyte concentration is proportional to the measured signal. In the detection process, the sensor thus ascertains a change in charge, which is caused by the reversible displacement of the antagonist 68 from the receptor 64 by the analyte 66. If the concentration of analyte 66 in the blood, and thus also in the interior of the sensor, decreases, primarily antagonists 68 again bind to the receptor 64, and the measurement signal at the seFET rises again. FIG. 2 also shows that the analytes 66 and antagonists 68 that have not bound precisely to the antigen recognition site of the receptor 64 do not contribute to the generation of the measurement signal.

The receptor layer applied to the gate of the seFET does not occupy all binding valences of the surface of the gate. Additional free or unsaturated binding sites 76 of the seFET that are still present must be saturated, so that interferences by other charged molecules, such as micromolecules 78, can be effectively prevented. A passivation layer 78 is therefore applied to the seFET, which is designed to saturate non-specific binding sites 76. The passivation layer 88 is formed by a polymer, such as polyethylene glycol (PEG).

To prevent fouling caused by contact with tissue or measuring substances, surfaces 14, 16 of the implant, such as surfaces 14 of lateral walls of the housing 56 of the biosensor, made of titanium, for example, or the outer surface 16 of the polymer membrane 26, are coated with a coating 12 (Formulation I, see below) or a plasma polymer layer by way of plasma polymerization. The coating 12 is shown only in the right portion of the illustration of FIG. 2 on the first sections of the polymer membrane 26 and an upper portion of the surface 14 of the housing 56 in an oversized manner.

The surfaces 14, 16 to be coated do not have a smooth surface. These have at least nanoroughness or are porous. Such surface properties or structures require a specially developed coating protocol to yield a coating 12 that adheres well and additionally has further advantageous properties (suppressing fouling, antibiotic property).

Four different coatings 12, 12', 12", 12''' having different formulations (Formulations I, II, III, IV) were generated (layer thickness 24 nm±2 nm) and analyzed for the suitability of the same. The differences in the formulations and the resulting layer properties can be derived from Table 1 below.

TABLE 1

Differences in the coating formulations and the resulting layer properties

| Formulation | Flow rates [sccm] | Growth rate [nm/min] | Atomic composition [%] ± 1 | | | | Roughness Rms [nm] |
|---|---|---|---|---|---|---|---|
| | | | C | O | N | Ti | |
| I | 2.5 CH$_4$ + 1.3 O$_2$ | 0.2 | 65 | 31 | 1.9 | 2.1 | 0.3 |
| II. | 2.8 CH$_4$ + 1.1 O$_2$ | 0.9 | 71 | 26 | 1.5 | 1.5 | 2.3 |
| III | 3.0 CH$_4$ + 1.0 O$_2$ | 1.2 | 72 | 24 | 2.5 | 1.5 | 2.4 |
| IV | 5.0 CH$_4$ | 2.0 | 89 | 9 | 2.0 | 0.0 | 0.4 |

Figure 3:
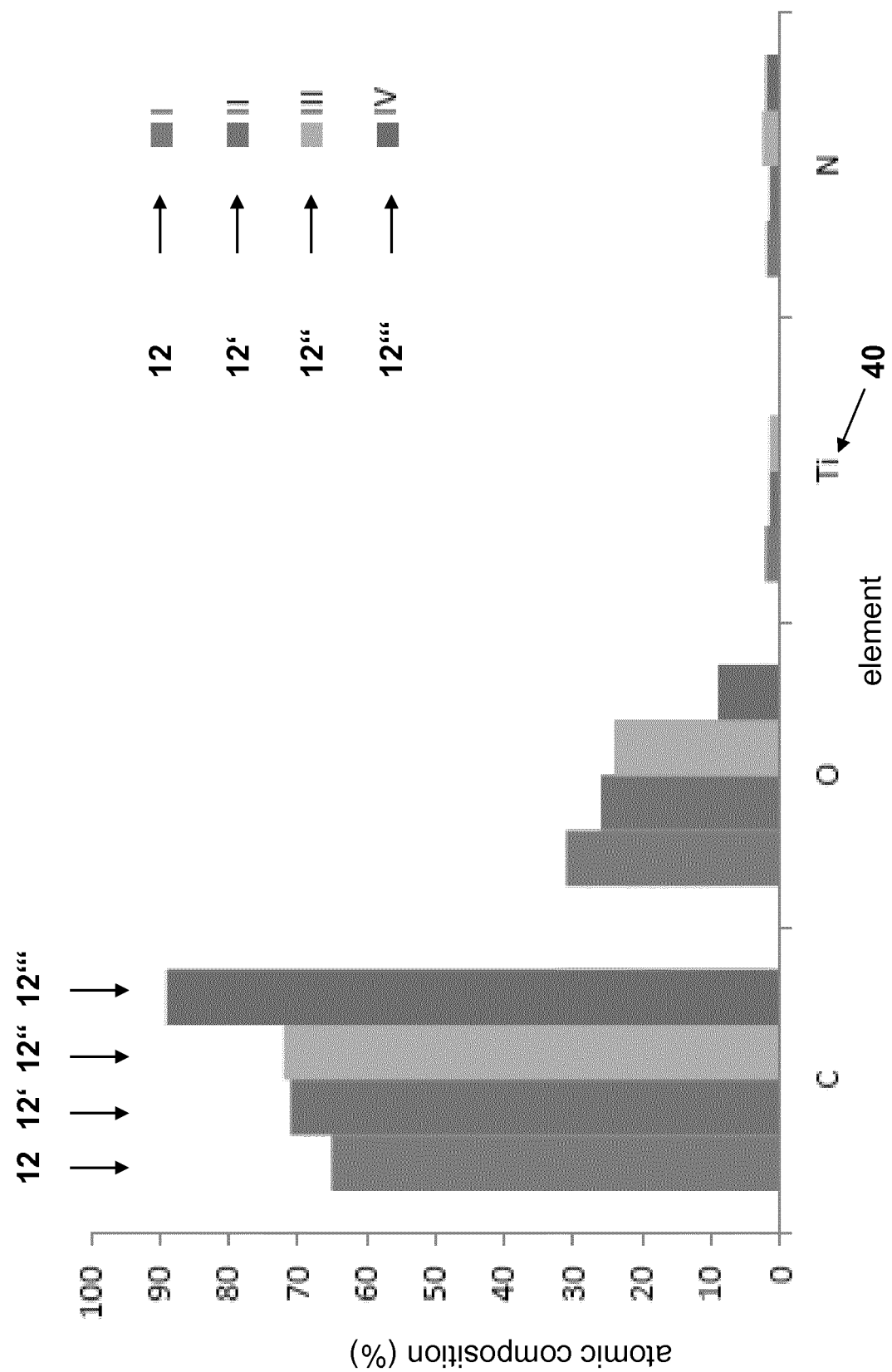
FIG. 3 shows a diagram representing the atomic composition of four different plasma polymer layers (Formulations I to IV), which were generated by way of the plasma polymer system of FIG. 1.

The atomic compositions of the four coatings 12, 12', 12", 12''' listed in Table 1 can also be seen in FIG. 3, which shows a diagram in which the chemical elements of the coatings 12, 12', 12", 12''' are plotted on the x axis, and the atomic compositions of the coatings 12, 12', 12", 12''' in % are plotted on the y axis. The respective first (left) bar shows the coating 12 according to Formulation I, the second bar shows the coating 12' according to Formulation II, the third bar shows the coating 12" according to Formulation II, and the fourth and last bar shows the coating 12''' according to Formulation IV.

Without being bound to this theory, it is assumed that nitrogen becomes embedded in the coating at the point in time at which the reactor, in which the plasma polymerization is carried out, is flooded after plasma polymerization, so that, after the plasma polymerization, the coating is surrounded by a nitrogen atmosphere, and more particularly an oxygen-free and/or waterless nitrogen atmosphere.

A discernible connection can be found between the formulations and the atomic compositions of coatings 12, 12', 12", 12'''. If the oxygen fraction is increased in the precursor gas, more oxygen is also integrated into the coatings 12, 12', 12", 12''', wherein the carbon fraction, in terms of percent, decreases. A look at the element titanium shows that the fraction thereof, in terms of percent, likewise increases as the oxygen fraction in the starting material increases. It can be assumed that primarily conglomerates composed of titanium and oxygen are embedded into the plasma polymer. No trend can be observed for the different formulations with respect to the element nitrogen.

An examination of the coatings 12, 12', 12", 12''' for the type of compounds or groups that are present in the plasma polymer based on a peak analysis shows the results listed by way of example in Table 2 for the coatings 12 and 12''' of formulations I and IV.

TABLE 2

Results of the peak analysis of coatings 12 and 12'''
of formulations I and IV

| Peak | $C_1$ | $C_2$ | $C_3$ | $C_4$ |
|---|---|---|---|---|
| Binding energy (eV) | 285.0 | 286.5 | 288.0 | 289.3 |
| Bond | C—C, and/or C—H | C—OH or C—O—C | —C═O | O—C═O |
| Formulation I | 4.7% | 61.3% | — | 34.0% |
| Formulation IV | 63.4% | 36.6% | — | — |

It was found that the $C_2$ component is of particular importance. A distinction must be made between the two possible groups of this component. Deliberations made, which are not described in greater detail here, result in the assumption that the $C_2$ component is primarily present in these coatings 12, 12', 12", 12''' in the form of a C—O—C bond. However, it is also possible for smaller amounts of C—OH bonds to be present. This means that essentially oxygen-containing hydrocarbon coatings are formed.

Another option for characterizing the surface properties is to examine the interaction of two media having different states of matter, which make contact with each other at the interface, for example based on a dynamic contact angle measurement. The result of this examination is shown in the diagram of FIG. 4, in which the Formulations I to IV of coatings 12, 12', 12", 12''' are plotted on the x axis, and the progressing contact angles $\Theta$ in ° is plotted on they axis.

Figure 4:
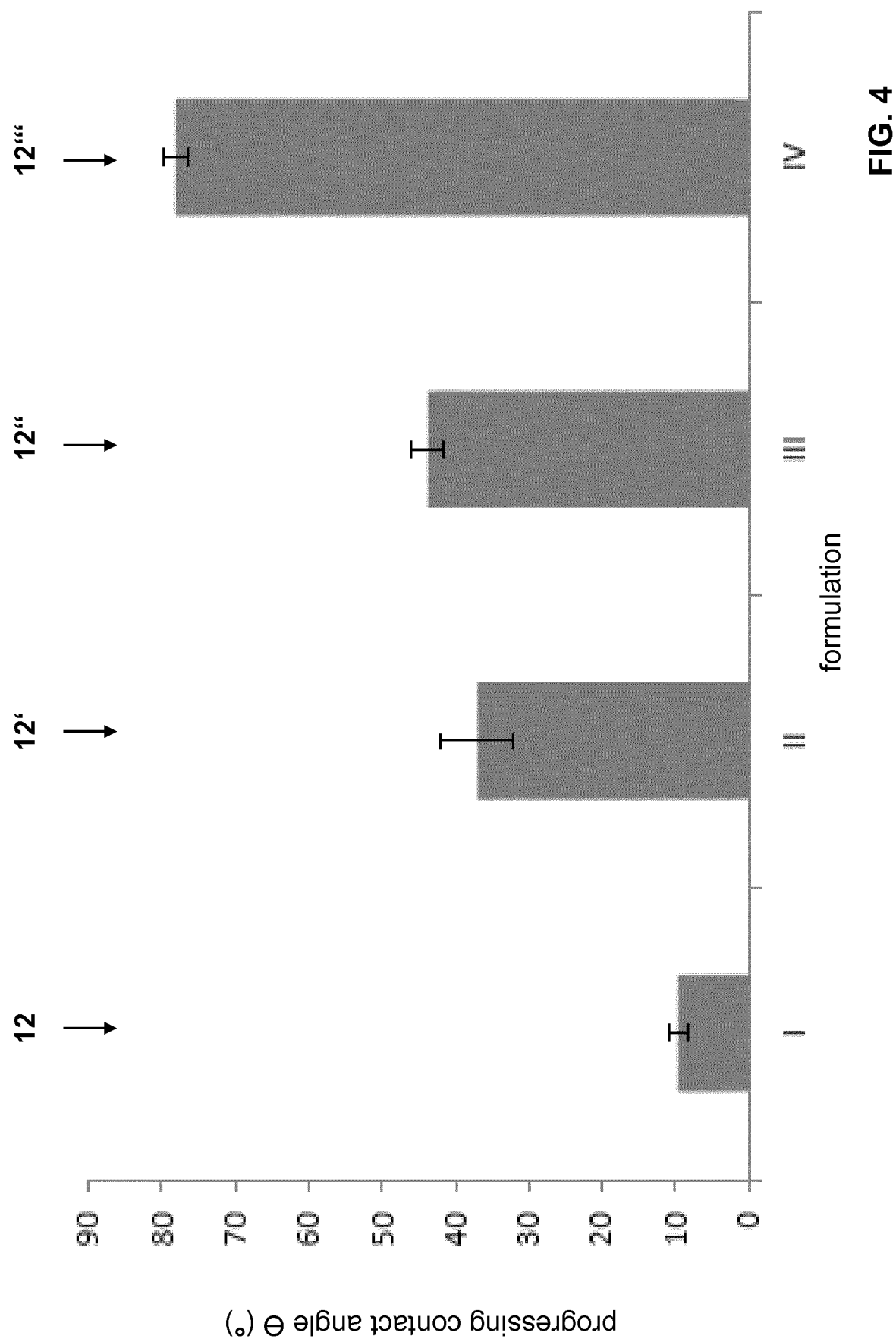
FIG. 4 shows a diagram illustrating a progressing contact angle as a function of a composition of respective used process gases.

As can be seen in FIG. 4, a relationship exists between the gas ratio of the starting material and the wetting property of the resulting coating 12, 12', 12", 12'''. The higher the oxygen fraction in the starting material, the lower is the contact angle $\Theta$. From this, it can be derived that the higher the oxygen content in the coating 12, 12', 12", 12''', the better is the wetting property. In other words, the higher the oxygen content in the coating 12, 12', 12", 12''', the greater is the hydrophilicity.

Figure 5:
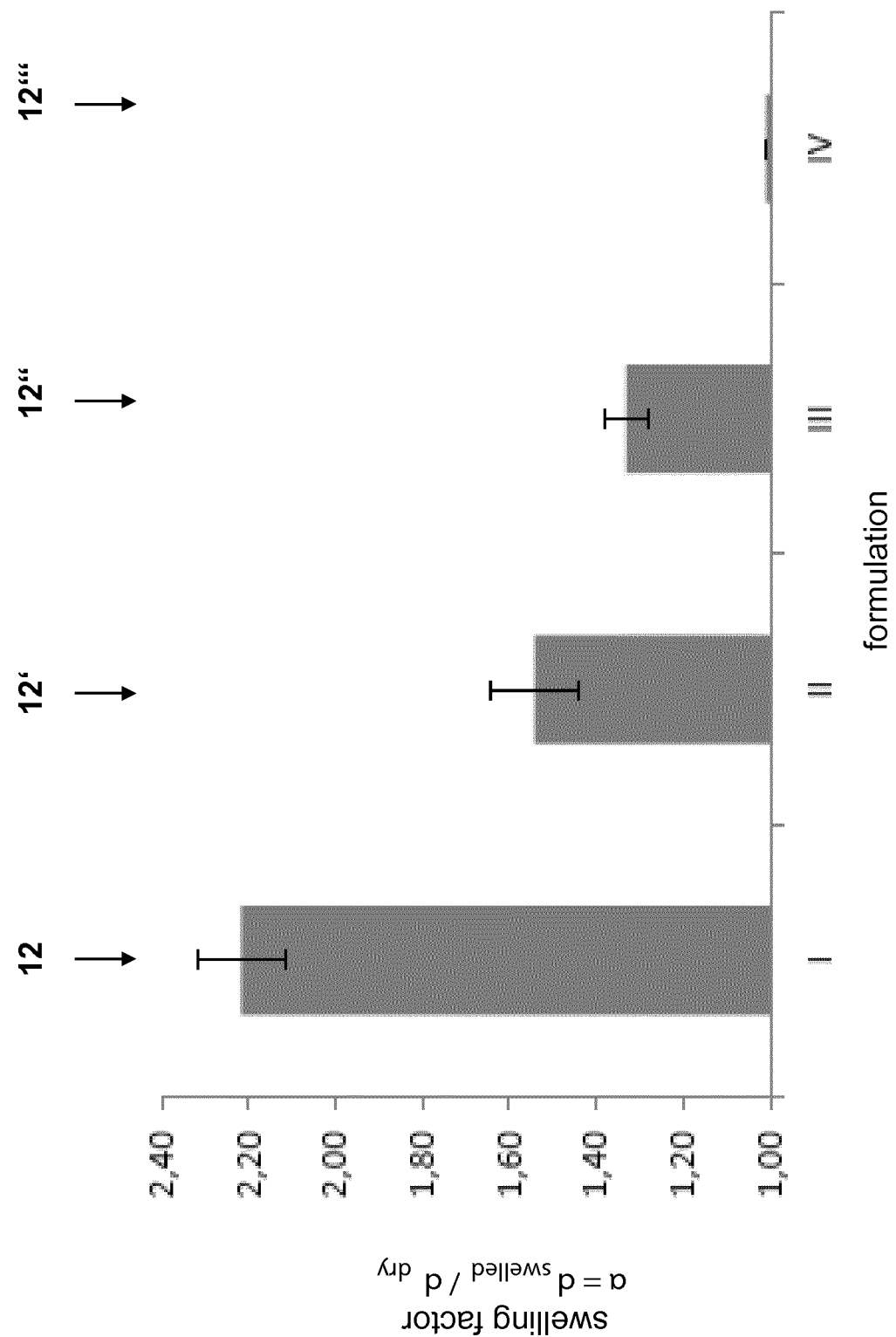
FIG. 5 shows a diagram illustrating a swelling factor as a function of a composition of respective used process gases.

To supplement the determination of the hydrophilicity, what is known as the swelling factor of the coatings 12, 12', 12", 12''' was ascertained. The result of this examination is discernible from the diagram of FIG. 5, in which the Formulations I to IV of coatings 12, 12', 12", 12''' are plotted on the x axis, and the swelling factor $\alpha = d_{swelled}/d_{dry}$ is plotted on the y axis. This measurement as well shows a distinct relationship between the composition of the coating 12, 12', 12", 12''' and the interaction of these plasma polymers with water, or swelling. Nanofilms having a high oxygen fraction have a swelling factor of up to 2.2 (coating 12); in plasma polymers having a very low oxygen fraction, almost no swelling exists (coating 12'''). The penetration of water, and the swelling associated therewith, decisively depend on the number of polar groups.

Figure 6:
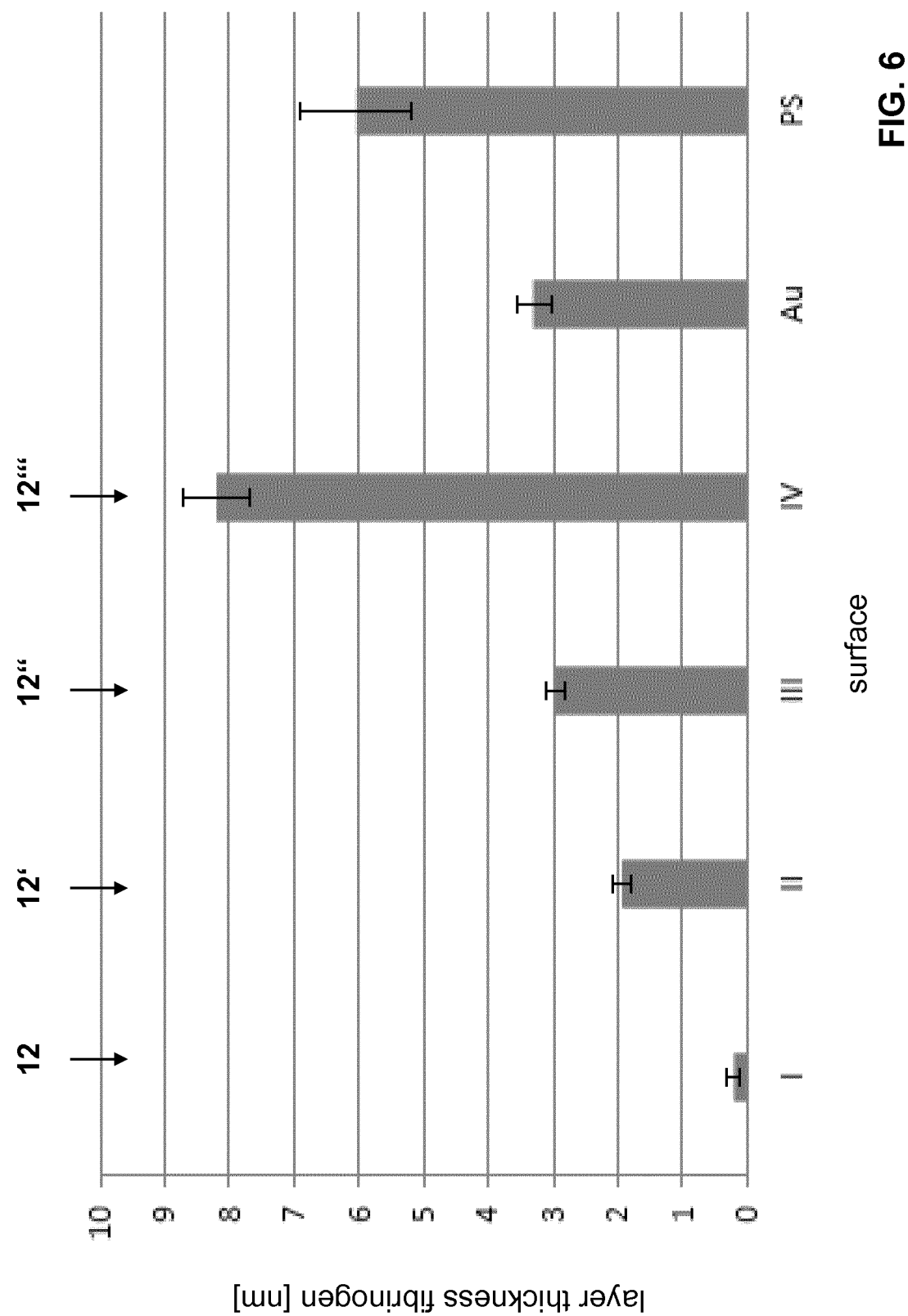
FIG. 6 shows a diagram illustrating the protein adsorption as a function of a composition of respective used process gases.

For the ascertainment of the non-specific protein adsorption of the coatings 12, 12', 12", 12''' was ascertained. For this purpose, the coatings 12, 12', 12", 12''' were incubated with the protein fibrinogen occurring in blood (2 mg/ml in PBS buffer), and thereafter the layer thickness of the adhering fibrinogen was ascertained by way of surface plasmon resonance spectroscopy. As can be seen in the diagram of FIG. 6, in which the Formulations I to IV of the coatings 12, 12', 12", 12''' as well as a gold coating (Au) and a polystyrene coating (PS), serving as references, are plotted on the x axis, and the layer thickness of the fibrinogen in nm is plotted on the y axis, a relationship is apparent between the particular nanofilm and the layer thickness of the adsorbed fibrinogen. The measurement results differ from each other, ranging from almost no protein on coating 12 using Formulation I to a layer thickness of 8.8 nm on coating 12''' according to Formulation IV. An uncoated gold surface and polystyrene were used as references. As described above, the coating 12 has a high oxygen content and a high swelling factor. This is associated with very low protein adsorption. The good water wetting property minimizes the hydrophobic interactions between the protein and the surface The chemical composition of the coating 12 has relatively high agreement with that of polyethylene oxide (PEO). This behavior is explained with the good interaction of these nanofilms with water with respect to PEO. The polar and nonpolar groups, which are located directly at the interface between the coating and the water, fit the lattice structure of water very well. This results in a stable structure or orientation of the water molecules on the surface, and thus in a disadvantageous energy balance of the protein adsorption.

It is further proposed for the coating to have a moderate swelling factor, preferably a swelling factor in the range of 1.2 to 3.5, and more preferably in the range of 1.5 to 3.0. The advantage of such a coating is that a swelling factor of this magnitude keeps the adsorption of the body's own proteins low, while the few proteins that do adsorb remain in the native conformal structure thereof. In this way, particularly effective masking of an implant by the body is achieved, which makes ingrowth of the implant more difficult or prevents the same, and thereby furthermore enables explantation without complications.

The adsorption of fibrinogen allowed the progression from an elevated amount of protein on surfaces low in oxygen to little protein on surfaces rich in oxygen to be tracked very well. The reduction in the amount of protein is associated with an increased degree of swelling and increasing hydrophilicity. It is now of interest to explore the structure in which the proteins are present after adsorption, and whether the secondary structure thereof is preserved. In this respect, a structure that is similar to the native structure in solution was able to be shown both for albumin and for fibrinogen on oxygen-rich coatings (not shown). Despite this native structure on the surface, it was not possible to wash these proteins off the surface; instead, they bind to the same. This native structure of the proteins on the surface represents the principle of good biological compatibility. They ultimately form the direct interface, and no foreign body reaction is triggered by virtue of the native structure. The proteins on the surface are bound firmly, wherein the hydrophilicity and swelling ensure that liquid surrounds the proteins on the surface and that the mobility of the polymer chains favors the formation of a bond with the protein, however that this bond does not exceed the intramolecular forces of the protein, and consequently as little a deformation of the proteins as possible occurs on the foreign body surface.

Figure 7:
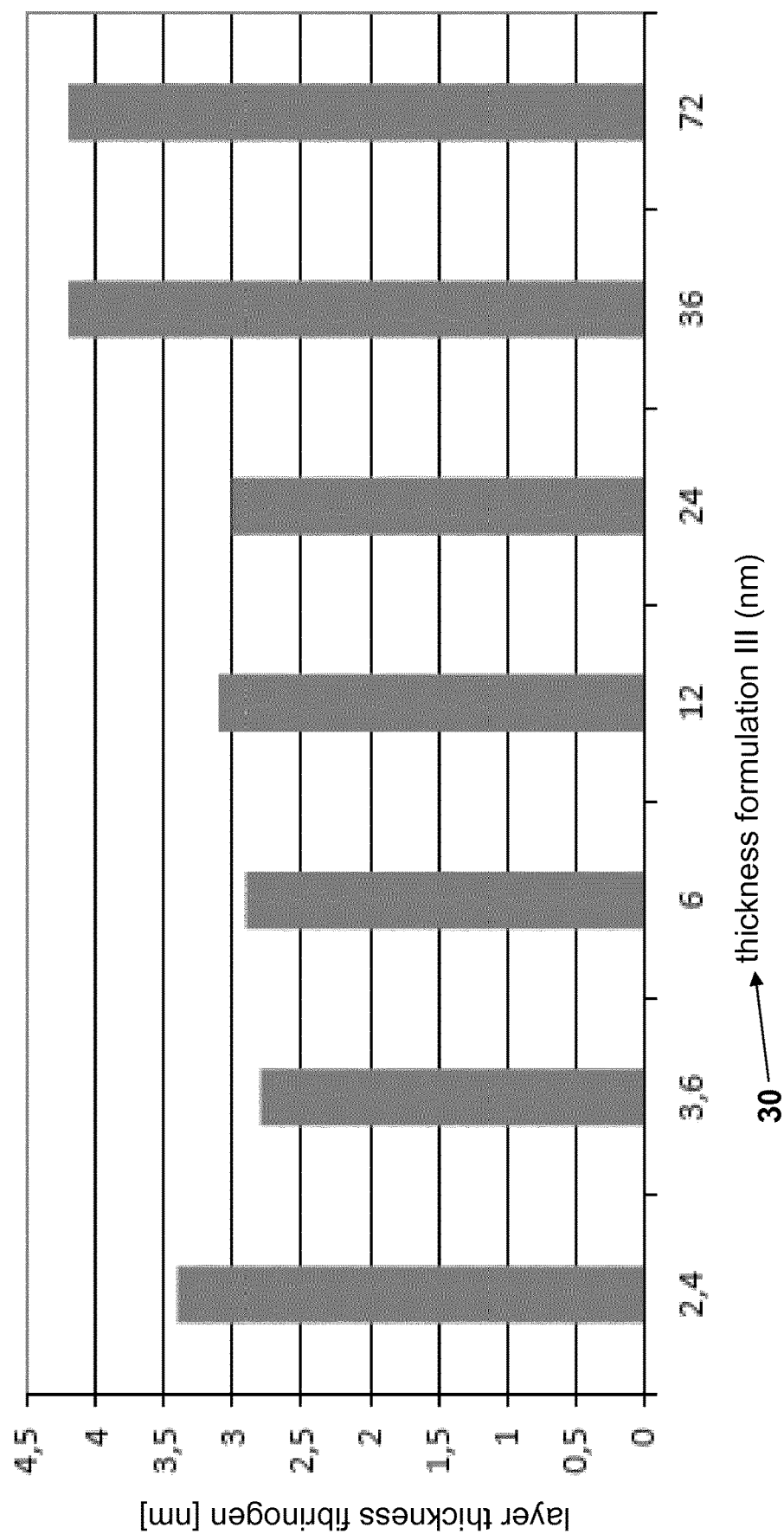
FIG. 7 shows a diagram illustrating the protein adsorption as a function of a layer thickness of the coating.

In addition, the influence of the layer thicknesses 30 of the coatings 12, 12', 12", 12''' on the adsorption of fibrinogen was examined. To obtain an adequate measurement range, these measurements were carried out using varying thicknesses of the coatings 12", produced according to Formulation III. The result is shown in the diagram of FIG. 7, in which the varying layer thicknesses 30 of the coating 12" according to Formulation III are plotted on the x axis, and the layer thickness of the fibrinogen in nm is plotted on the y axis. The measurement results show a constant layer thickness of the adsorbed fibrinogen at layer thicknesses 30 of the coating 12" between 3.6 nm and 24 nm.

It is assumed that low or no protein adsorption can be equated to good biocompatibility. The low adsorption of fibrinogen on the coating 12, produced according to Formulation I, was therefore taken as an opportunity to provide the implant 10, or the surfaces 14 and 16, with such a coating 12. For this purpose, the coating parameters were, or coating time was, selected so that a layer thickness 30 of 15 nm to 25 nm was deposited (see FIG. 2). A coating time of approximately 60 min was sufficient for this purpose.

The surfaces 14 of the housing 56 of the implant 10, which can be introduced into a bloodstream of an animal body and/or a human body, were coated using the following coating parameters: pressure: 5 Pa, flow rate of the methane coating gas 18: 2.5 sccm, flow rate of the oxygen coating gas 20: 1.3 sccm, current intensity of the plasma polymerization system 22: 200 mA, electrodes 24 of the plasma polymerization system 22: 100% titanium, rotational speed of the sample holder 50: 2 rpm, and coating duration 1 to 200 min, preferably 20 min to 100 min, and particularly preferably 60 min.

Figure 8:
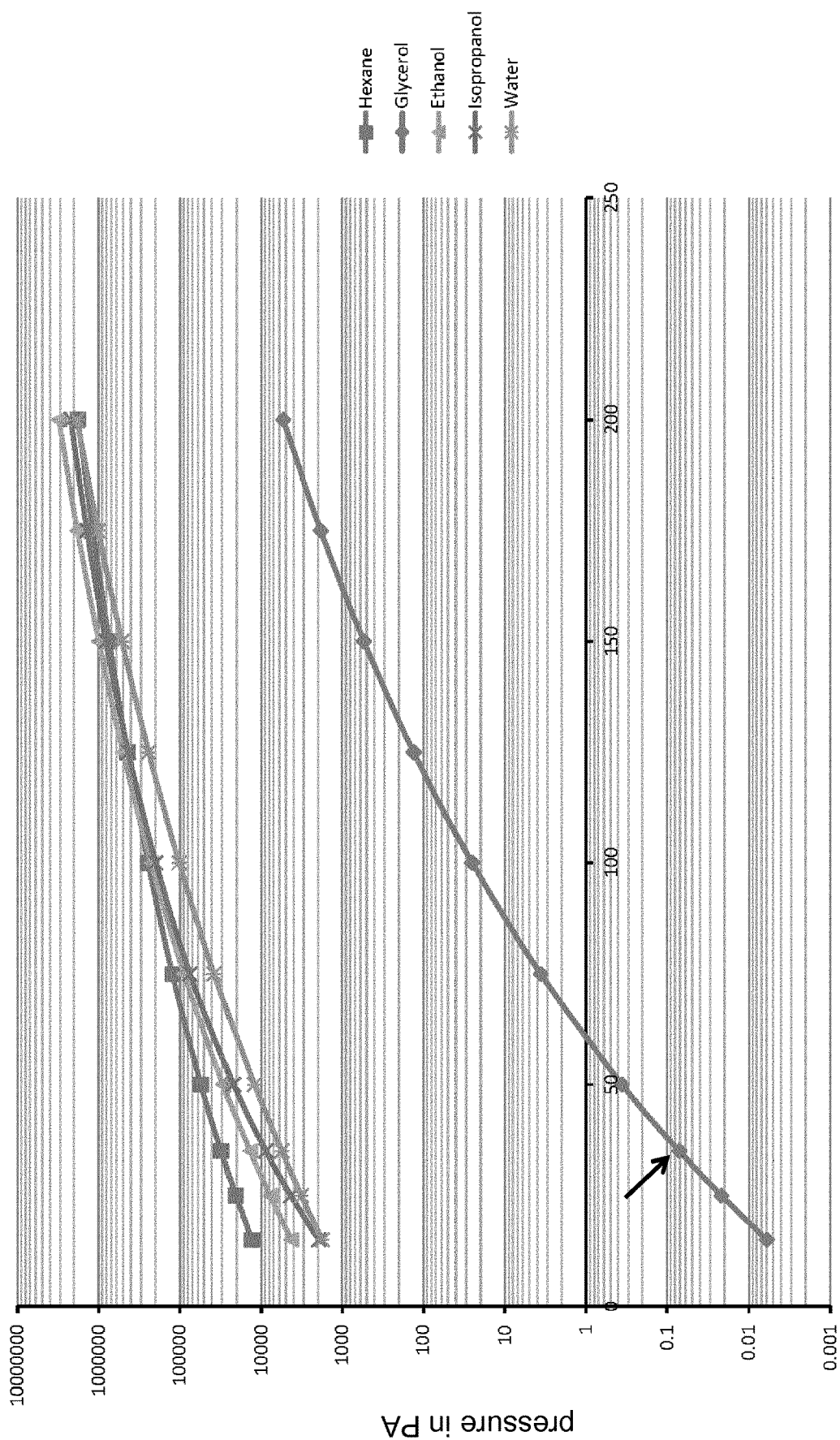
FIG. 8 shows a diagram illustrating a vapor pressure curve of different substances and of glycerol as a function of a temperature.

In the coating of the surface 16 or of the polymer membrane 26, it had to be taken into consideration that the pores 28 of the polymer membrane 26 are stabilized with a stabilizer 42 in the form of glycerol to prevent collapsing on air (In FIG. 2, indicated only for one pore 28). This glycerol must still be intact after the coating process. Accordingly, the coating process must be deliberately adapted. The coating parameters are selected so that the glycerol on the surface of the membrane 26 is evaporated, and the glycerol in the pores 28 is preserved, prior to applying the plasma polymer layer 12. In this way, the surface 16 of the membrane 26 may be coated with plasma polymers, while the stabilizer 42 remains preserved in the pores 28. This was successfully achieved by optimizing the method parameters, in which the glycerol on the surface 16 of the membrane 26 is removed, not however in the pores 28. This approach takes advantage of the fact that the vapor pressure of glycerol is in the pressure range that prevails or is set during the coating process in the plasma polymerization system. This is discernible from the diagram of FIG. 8, in which the temperature in ° C. is plotted on the x axis, and the pressure in Pa is plotted on the y axis, and the vapor pressure curves of various substance are shown (pairings: symbol—substance: squares—hexane, diamonds—glycerol, triangles—ethanol, crosses—isopropanol, stars—water). It can be seen that the vapor pressure of glycerol (diamond symbol) is in the range of the optimized pressure generated in the chamber (arrow). As a result, the glycerol is evaporated in the reaction chamber of the plasma polymerization system 22.

For the actual coating process of the membrane 26, the sample is mounted on the sample holder 50 as is customary. Thereafter, the vacuum is generated by the butterfly valve to the vacuum pump being opened (not shown in detail). The optimized vacuum cycle is influenced by way of the pumping capacity, among other things. The glycerol thus begins to evaporate due to the vapor pressure. This can be observed based on a curve progression of the pressure in the coating chamber of the plasma polymerization system 22 when evacuating the coating chamber.

Figure 9:
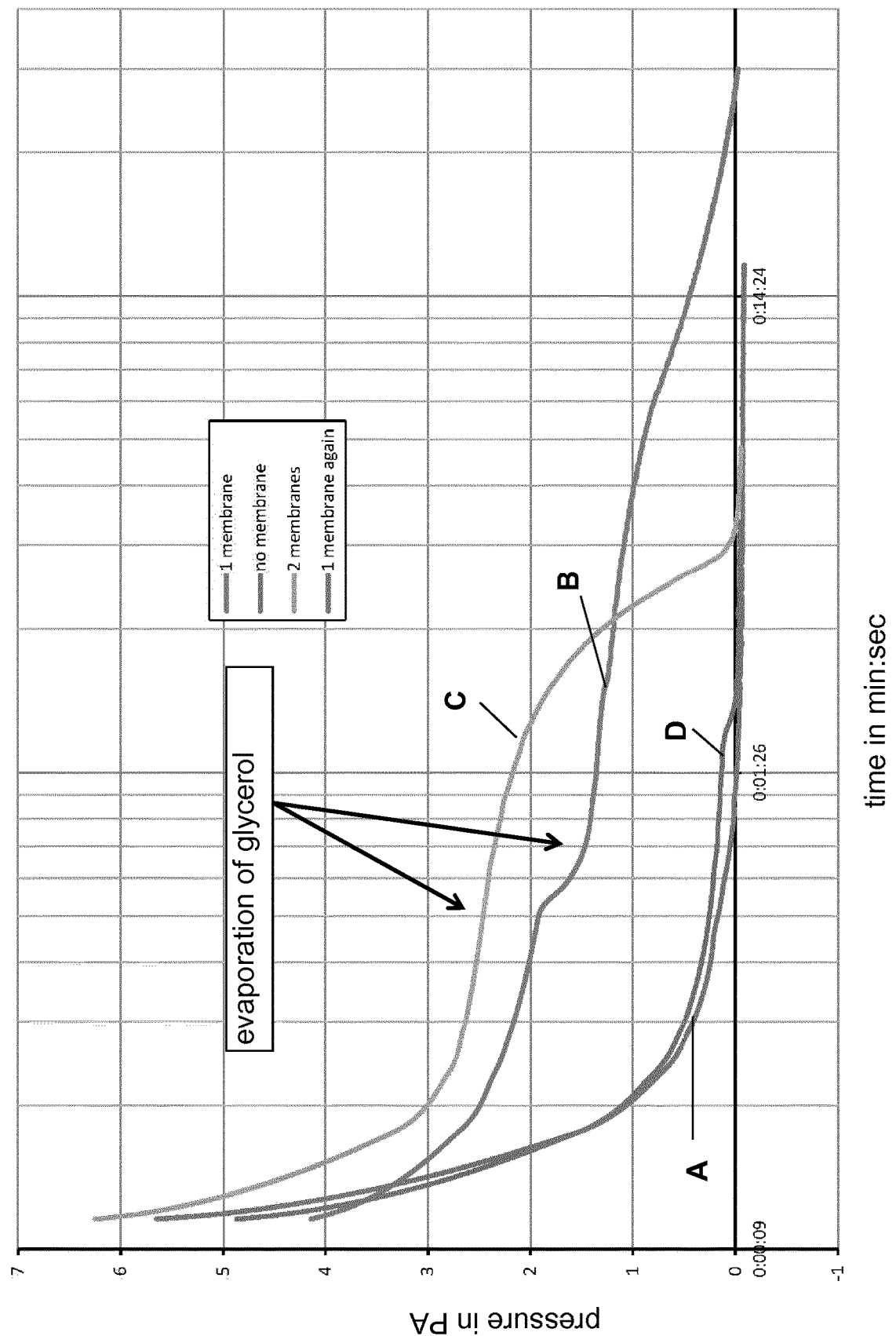
FIG. 9 shows a diagram illustrating a pressure measurement of four different arrangements in the plasma polymer system of FIG. 1.

A curve progression of the pressure as a function of the time is shown in the diagram of FIG. 9, in which the time in min:sec is plotted on the x axis, and the pressure in Pa is plotted on the y axis, for four different loadings (A, B, C, D) of the coating chamber. Loading A represents an evacuation of the coating chamber without the presence of a membrane, loading B represents the presence of a membrane 26, loading C represents the presence of two membranes 26, and loading D represents the presence of one membrane 26 where previously the glycerol was already evaporated (using the same process).

When a membrane 26, which is stabilized with glycerol, is introduced into the coating chamber (curve B), it is apparent compared to a reference measurement without membrane (curve A) that the time until the final pressure is achieved is reached not until after a long time period (see arrow). Based on the shape of the curve progression with membrane 26 (curves B and C), a clearly reduced gradient at the beginning of the process is apparent. In the case of multiple membranes (curve C), the "belly" of the curve becomes larger since more glycerol is being evaporated. The curve progression for loading D, in which the glycerol of the membrane 26 was already evaporated in advance, is similar to that of the control without membrane in the coating chamber (curve A). The shape of the membrane is observed as a control measure to ensure that the amount of glycerol that was evaporated is not excessive—the membrane 26 would bend if a loss of glycerol in the pores 28 were to occur. When a constant final pressure is reached, the plasma polymer coating commences.

It has been shown that such a polymer membrane 26 can be coated using the following coating parameters: pressure: 1 Pa to 3 Pa, flow rate of the methane coating gas 18: 2.5 sccm, flow rate of the oxygen coating gas 20: 1.3 sccm, current intensity of the plasma polymerization system 22: 100 mA to 400 mA, for example 375 mA, electrodes 24 of the plasma polymerization system 22: 100% titanium, rotational speed of the sample holder 50: 2 rpm, and coating duration 1 min to 200 min, preferably 60 min to 160 min, particularly preferably 140 min. A good layer thickness 30 of approximately 15 nm to 25 nm can be achieved with a coating time of 140 min. The coating protocol differs slightly from the above-described protocol for Formulation I and is denoted by Ia.

Accordingly, the coating parameters were selected so that it was possible to coat a rough surface 14, 16. In addition, the coating parameters were selected so that it was possible to coat a surface 16 having permeability, which is to say the polymer membrane 26. Furthermore, to obtain the coating 12 according to Formulation I, the coating parameters were selected so that an oxygen-containing hydrocarbon coating 12 is formed.

Figure 10:
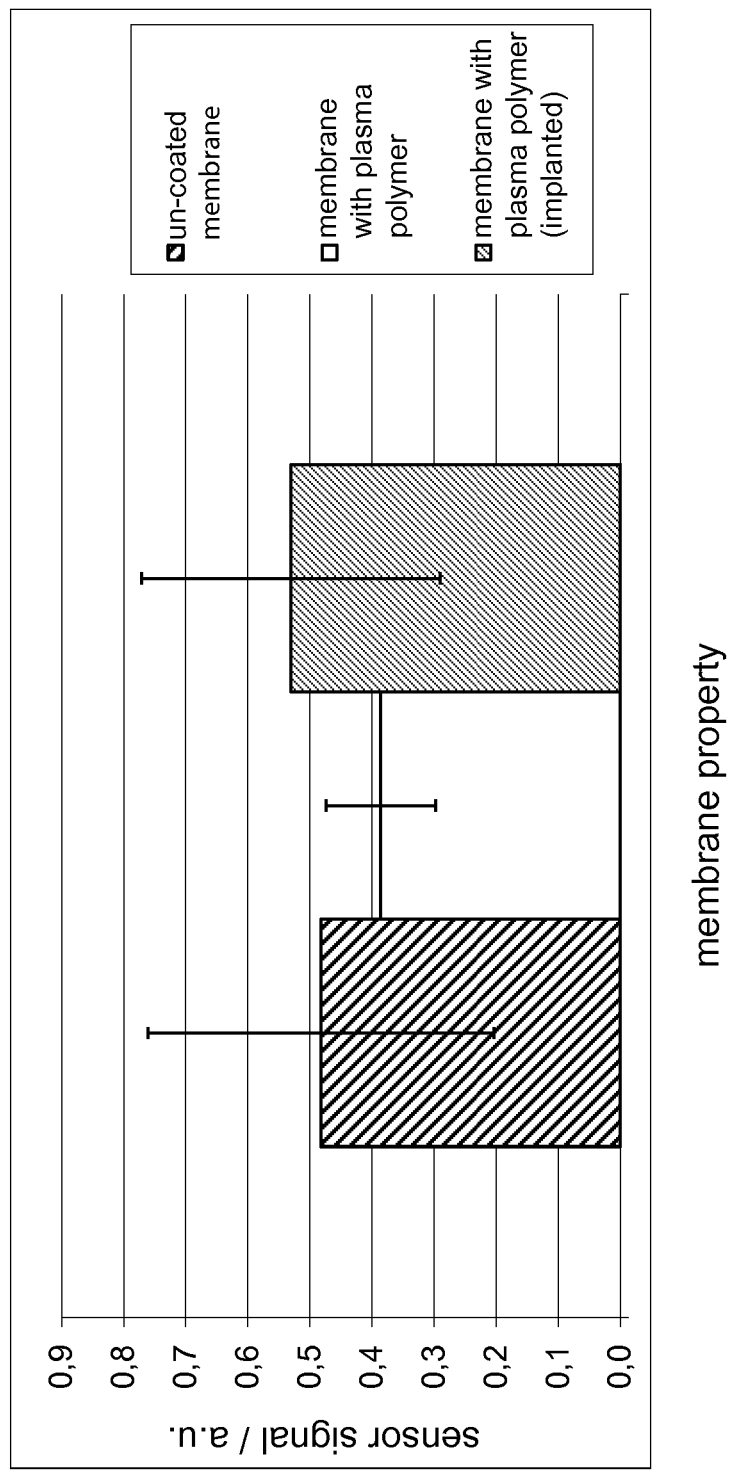
FIG. 10 shows a diagram illustrating a sensor signal of a polymer membrane of the biosensor of FIG. 2 for three differently treated polymer membranes.

The coated polymer membrane 26 of the implant 10 was subjected to a functional test. In this test, the permeabilities of the coated biosensor or of the polymer membrane 26 thereof were compared to those of an uncoated sensor. In addition, the permeability of a coated membrane 26 was examined after explantation in an in vivo incubation. As can be seen in the diagram of FIG. 10, in which the membrane property is plotted on the x axis, and a sensor signal is plotted on the y axis, the sensor signal of the coated implant 10 (white bar in the middle) does not differ significantly from the sensor signal of the uncoated implant (left bar with thick stripes). Even after implantation or explantation (right bar with thin stripes), the sensor signal remains substantially the same compared to the coated condition without implantation (white bar in the middle) and the uncoated condition (left bar with thick stripes). It was therefore possible to successfully demonstrate that the polymer membrane 26, and thus the biosensor, is intact and fully functional even after the coating process. It is also apparent from the figure that, in contact with body fluids, the membrane pores 28 remain passable to the analyte 66 to be detected, and the plasma polymer coating 12 thus also maintains its function in vivo.

The application of a plasma polymer layer having the above-described positive properties is only possible with difficulty on some substrates. This may be remedied by pretreating the surface 14, 16 to be coated. For example, one or more adhesion-supporting layers could be applied. To this end, an adhesion promoter layer 32 is applied as a mediating layer between the surface 14, 16 of the implant 10 which is to be coated and the plasma polymer layer or the coating 12, 12', 12", 12'''. This is shown by way of example in FIG. 2 on the left surface 14 of the implant 10. The properties of the adhesion promoter layer 32, and thus the coating parameters, are selected so that a subsequent application of the layer 12 can be carried out successfully, and in particular the positive properties are imparted to the same.

The coating with the adhesion promoter layer 32 is carried out using the following coating parameters: pressure: 5 Pa, flow rate of the methane coating gas 18: 2.5 sccm to 5 sccm, flow rate of the oxygen coating gas 20: 0 sccm to 2 sccm, current intensity of the plasma polymerization system 22: 200 mA, electrodes 24 of the plasma polymerization system 22: 100% titanium, rotational speed of the sample holder 50: 2 rpm, and coating duration 1 min to 200 min. By coating the surface 14 with an adhesion-promoting layer or with adhesion-promoting layers (referred to as layer stacks), the plasma polymers can be applied to any conceivable substrate.

A protocol having the following coating parameters has proven useful for applying the coatings 12, 12', 12", 12''' to the adhesion promoter layer 32: pressure: 5 Pa, flow rate of the methane coating gas 18: 2.5 sccm, flow rate of the oxygen coating gas 20: 1.3 sccm, current intensity of the plasma polymerization system 22: 200 mA, electrodes 24 of the plasma polymerization system 22: 100% titanium. rotational speed of the sample holder 50: 2 rpm, and coating duration 1 min to 200 min, preferably 20 min to 100 min, and particularly preferably 60 min.

When using implants such as the implant 10/biosensor described here, it is also desirable, in addition to minimizing accumulations of interfering substances 72 and a resulting encapsulation, to reduce, or even entirely prevent, an adherence of bacteria and the attendant inflammation at the implantation site. Accordingly, the four coatings 12, 12', 12", 12''', produced according to Formulations I to IV, were examined with respect to the antibiotic action thereof, which is to say the action thereof to inhibit or prevent bacterial growth. For this purpose, the adhesion of the bacteria on the different coatings 12, 12', 12", 12''' (applied to a silicon substrate, which also serves as a positive control) was ascertained over a time period of 24 hours.

Figure 11:
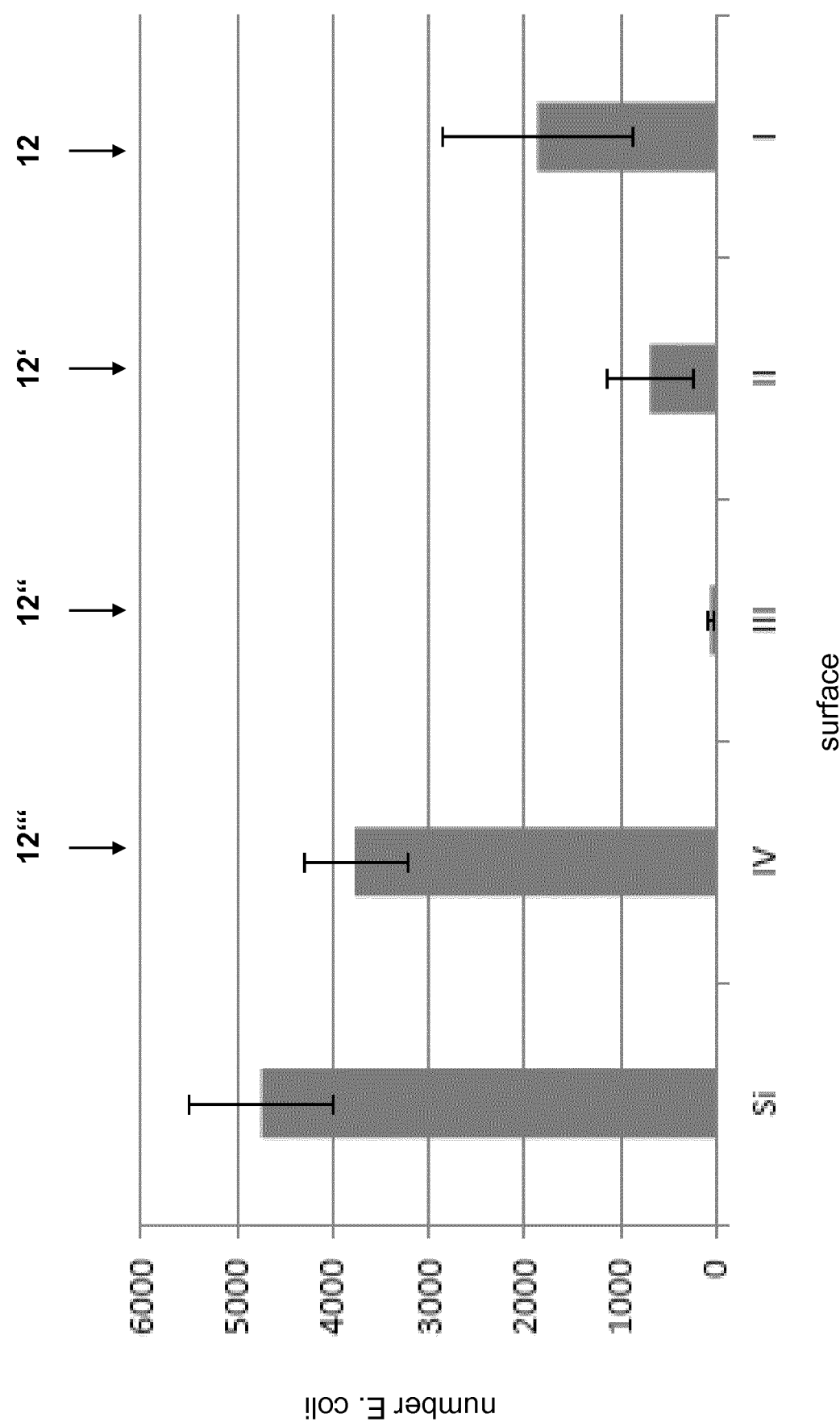
FIG. 11 shows a diagram representing the colonization with E. coli bacteria as a function of the type of colonized coating.

As can be seen in the diagram of FIG. 11, which shows the colonization with *E. coli* bacteria as a function of the type of the colonized coating 12, 12', 12", 12''', considerable differences can be found in the adhesion of *E. coli* bacteria to the different coatings 12, 12', 12", 12'''. The positive silicon control (left bar) contains the maximum of adhering bacteria. Considerable adhesion can also be found on the coating 12''' according to Formulation VI. The lowest colonization is found on coating 12", applied using Formulation III, wherein the coatings 12' (Formulation II) and 12 (Formulation I) likewise have a considerable reduction in adhering bacteria. Compared to the positive control, a value of 98.7% can be reported in terms of the reduction of bacteria on coating 12" according to Formulation III.

Figure 12:
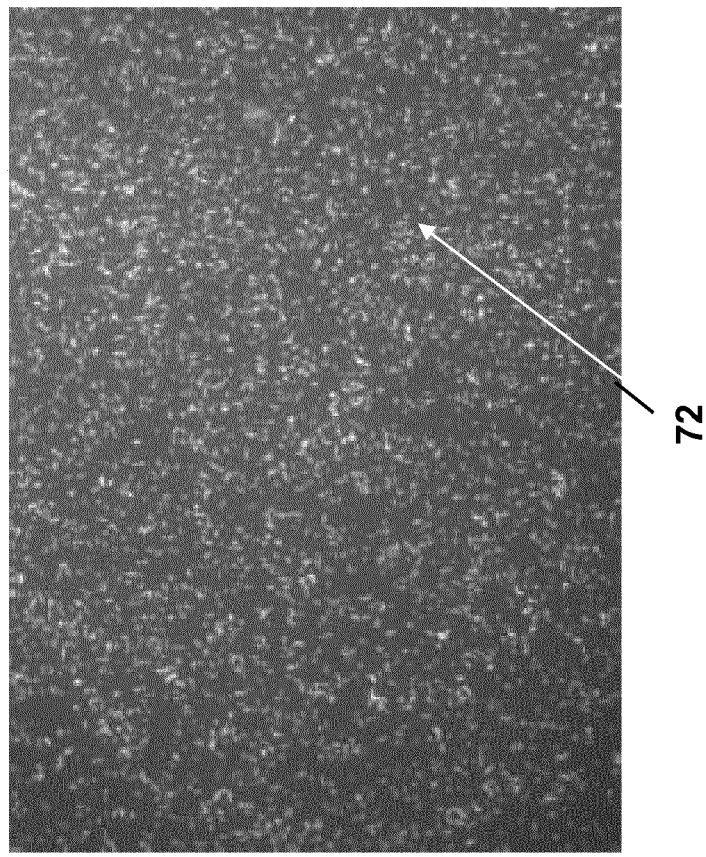
FIG. 12 shows a microscopic image with a 1:200 magnification of an uncoated silicon surface having high bacterial colonization.
Figure 13:
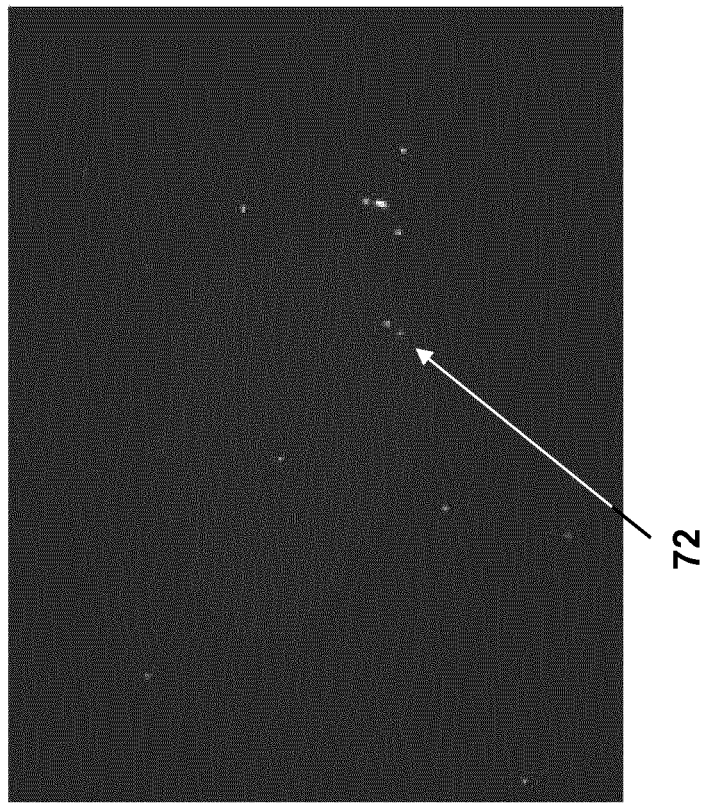
FIG. 13 shows a microscopic image with a 1:200 magnification of a silicon surface coated with a coating according to Formulation III of FIG. 3 having low bacterial colonization.

The difference in bacterial adhesion can also be seen well in the fluorescence microscopy images of GRP (green fluorescent protein)-marked bacteria 72 (magnification 1:200) of FIGS. 12 and 13. As can be seen in FIG. 12, which shows a bacterial colonization of an uncoated silicon substrate, a high level of colonization occurs here (number of bacteria 72 per substrate 7265). In contrast, as is shown in FIG. 13, only minimal colonization takes place on a substrate coated with coating 12" (number of bacteria 72 per substrate 12).

Figure 14:
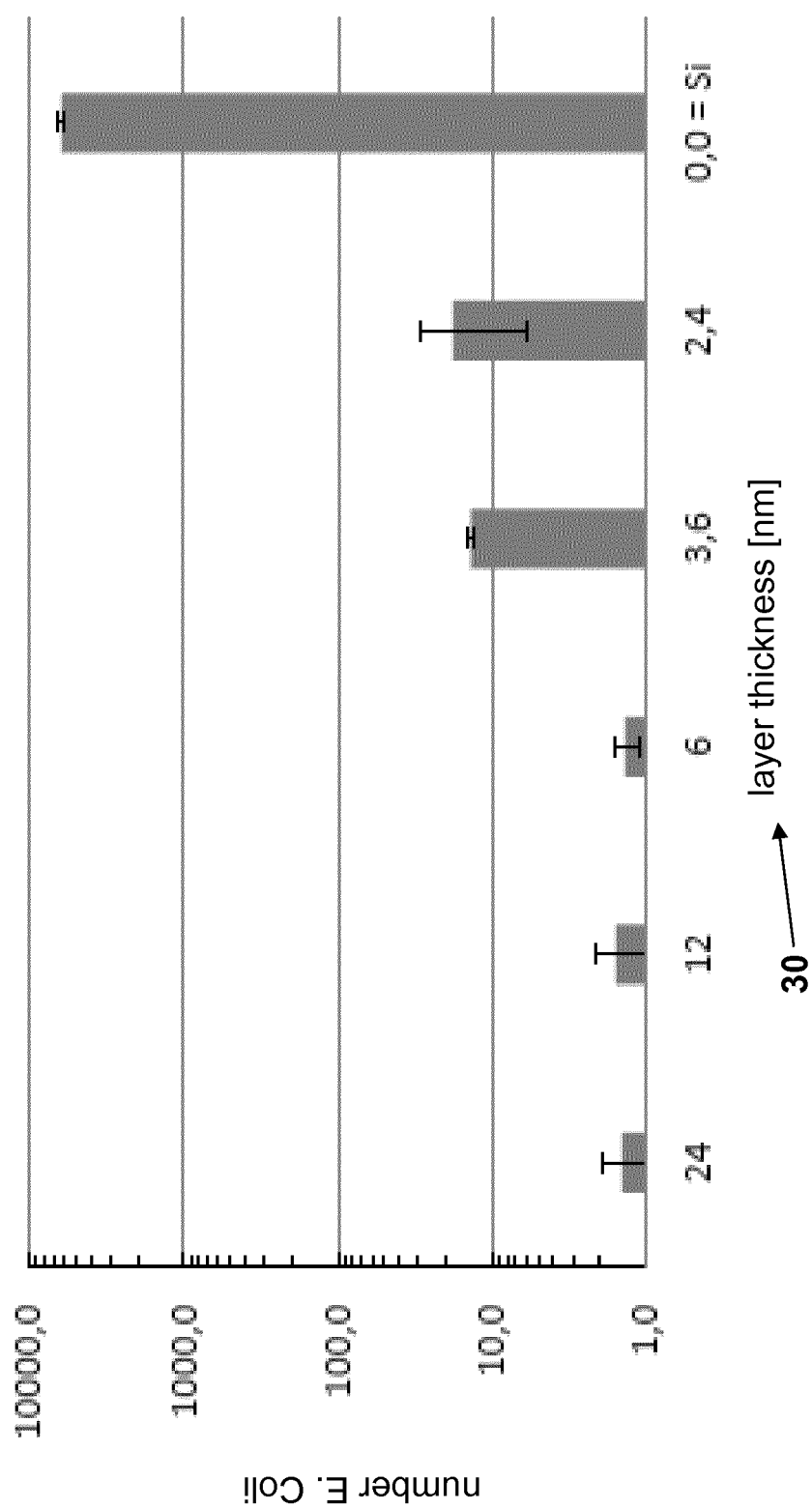
FIG. 14 shows a diagram illustrating the colonization with E. coli bacteria as a function of a layer thickness of the coating.

When examining the influence of the layer thickness 30 of the coating 12" according to Formulation III on the adhesion of bacteria, the results shown in the diagram of FIG. 14 are obtained, which illustrate the colonization with *E. coli* bacteria as a function of a layer thickness 30 of the coating 12". An uncoated silicon substrate (right bar) again serves as the reference.

Starting at a layer thickness 30 of 24 nm (left bar), a reduction in the number of bacteria on the coating 12" of 99% can likewise be seen. This value holds up to a layer thickness 30 of 6 nm. It is only starting at a layer thickness 30 of 3.6 nm and 2.4 nm that more bacteria can be found on the surface. This involves insular growth, where polymerized species or clusters, resembling the later nanofilm in terms of the properties of the same, form on the surface. These clusters already influence the settling of bacteria, but cannot prevent growth across the entire area. It has thus been shown that the antibacterial property of the coating 12" only occurs starting at a layer thickness of 6 nm.

These results were now used to coat the implant 10 such that a coating 12, 12', 12", 12''' having antibiotic properties is obtained. For this purpose, the following coating parameters were used: pressure: 1 Pa to 10 Pa, flow rate of the methane coating gas 18: 1 sccm to 5 sccm, flow rate of the oxygen coating gas 20: 0.5 sccm to 2 sccm, current intensity of the plasma polymerization system 22: 100 mA to 300 mA, coating time 1 minute (min) to 200 min, electrodes 24 of the plasma polymerization system 22: titanium, titanium content: >50%, rotational speed of the sample holder 50: 0 rpm to 5 pm.

Particularly good results were achieved using the following coating protocol: pressure: 4 Pa to 6 Pa, flow rate of the methane coating gas 18: 3 sccm, flow rate of the oxygen coating gas 20: 1 sccm, current intensity of the plasma polymerization system 22: 150 mA to 250 mA, coating time: 1 min to 200 min, electrodes 24 of the plasma polymerization system 22: titanium, titanium content: 100%, rotational speed of the sample holder 50: 2 rpm.

It was found that the antibiotic action of the plasma polymer layers is based on titanium becoming embedded in the polymer layer. The coating parameters are thus selected such that at least one antibiotically acting metal 40 is introduced into the coating 12, 12', 12", 12'''. The fact that this takes place during the plasma polymerization process is apparent from the resulting atomic compositions of the coatings 12, 12', 12", 12''' (see Table 1 and FIG. 3). This can be achieved by applying the coating 12, 12', 12", 12''' in the presence of at least one antibiotically acting metal 40, and more particularly by knocking the antibiotically acting metal 40 out of the electrodes 24 of the plasma polymerization system 22 during the coating process.

As described above, a wide variety of collisions, such as excitation, ionization and recombination of the involved species, take place in the plasma during plasma polymerization. Likewise, electrode material (such as titanium) is "sputtered out" during these processes, which is then likewise embedded in the nanofilm/the coating 12, 12', 12'', 12'''. If the parameters are selected correctly, a polymer is formed from the starting substances, this being methane and oxygen, and titanium becomes embedded therein. During the incorporation of titanium oxide into the polymer network, photocatalysis takes place as a result of UV light or near-UV light. This photocatalysis can already take place during the process. This, in turn, leads to the formation of oxygen radicals, which have a damaging effect on bacteria 72. The photocatalysis then forms radicals, which can destroy bacteria 72. Even if the coating is stored under dark conditions directly after the coating process, the surface remains antibacterial.

As is apparent from FIG. 2 and the description above, it is possible for only individual surfaces 14, 16 of the implant 10 to be coated. The coatings 12, 12', 12'', 12''' may also differ from each other, or adhesion promoter layers 32 may be used on certain surfaces 14. To yield sectional and/or only partial coating, regions that are to remain uncoated can be covered during the coating process.

An embodiment comprising coated and uncoated regions may even be advantageous, since these regions can individually assume different functions. For example, if the implant 10 comprises a functional sector 36 in the form of an analysis sector, such as the sensor system 54, it is advantageous to coat this analysis sector or functional sector 36 to suppress fouling, which may interfere with the measurement process or render it impossible. If the implant 10 moreover comprises an attachment sector 38, it may be useful to leave the same uncoated (see FIG. 2). In this way, the implant 10 can be attached by an encapsulation of the attachment sector 38 or anchored in the tissue.

Moreover, a compatibility of the implant 10 can be improved by sterilizing the implant 10, and more particularly by way of ethylene oxide. This is particularly advantageous, since the coating 12 or plasma polymer coatings can also be sterilized by way of ethylene oxide, without impairing the structure or properties of the same.

It was even shown that the properties of the plasma polymer layers improve as a result of the treatment with ethylene oxide. The coatings 12, 12', 12'', 12''' exhibit an aging process when stored on air. During this aging process, slowly increasing contact angles Θ develop over the course of weeks. This is caused by translatory movements of polar groups in the polymer matrix. In a nonpolar environment (air), these groups become oriented in the direction of the bulk or in the polymer network. This manifests itself in an increased contact angle Θ. This aging process can be reversed by storing this coating 12, 12', 12'', 12''' in a polar liquid (such as water) (revitalization process). The preceding paragraphs explained that hydration of the plasma polymer layer is needed for the positive effects of the coating 12, 12', 12'', 12'''. In contact with water, the hydration of the layer can be observed based on the contact angle Θ. It was possible to demonstrate that sterilization by way of ethylene oxide particularly advantageously affects this "revitalization process."

Figure 15:
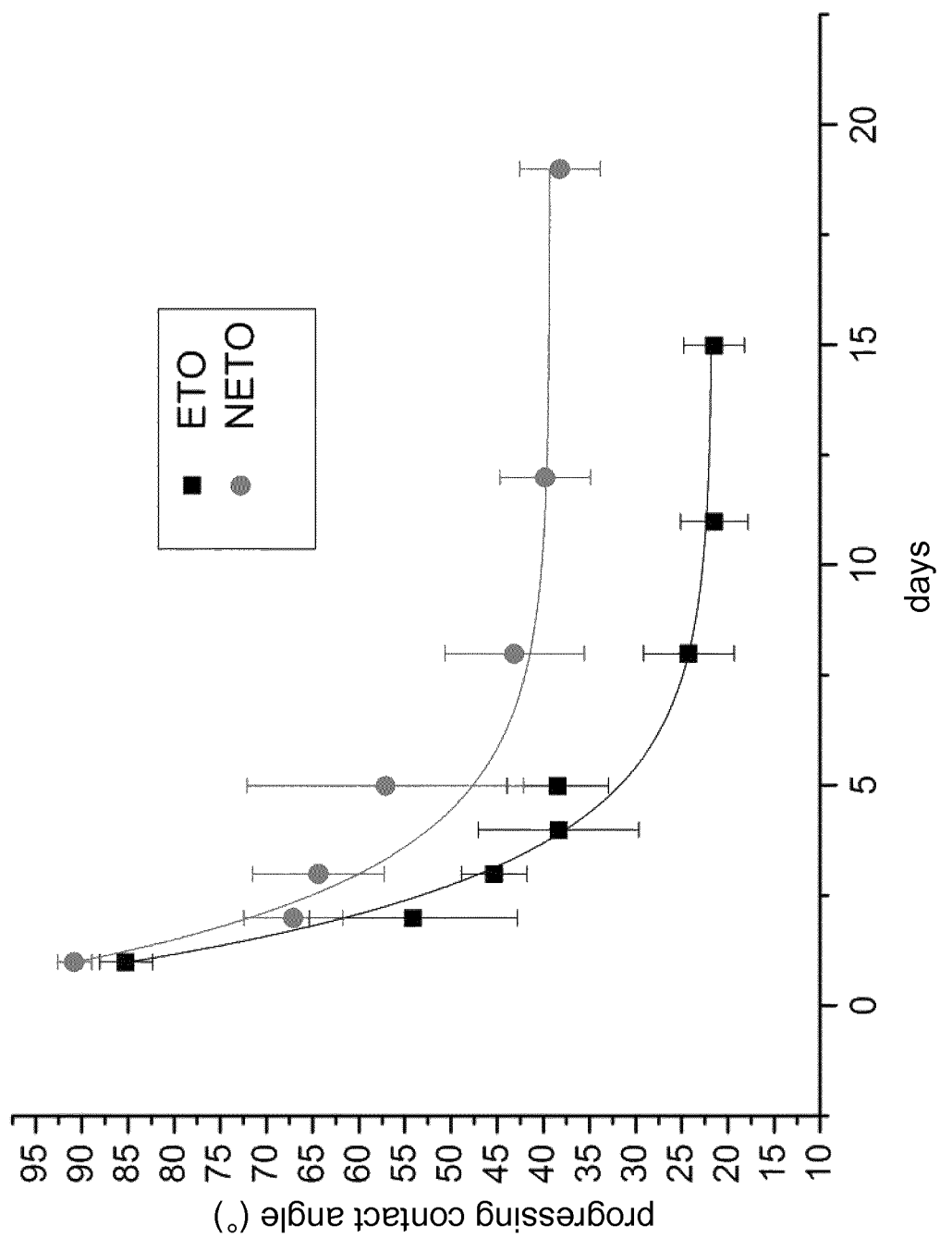
FIG. 15 shows a diagram illustrating the progressing contact angle as a function of the time for a sterilized coating and a non-sterilized coating.

As can be seen in the diagram of FIG. 15, in which the time in days is plotted on the x axis, and a progressing contact angle Θ is plotted on the y axis, the progression of the contact angle Θ as a function of the time differs for a coating 12 with ethylene oxide sterilization (squares) and a coating 12 without ethylene oxide sterilization (circles). Compared to the non-sterilized samples (circles), the required contact angles Θ are achieved more quickly in the sterilized samples (squares), and it is also apparent that even smaller contact angles Θ can be achieved by way of ethylene oxide sterilization. It can be assumed that the positive effects of the plasma polymer coating can be enhanced even further by a sterilization by way of ethylene oxide.

As a result of the physicochemical properties of the surfaces 14, 16 of the implant 10, no encapsulation of the implant 10 in collagen-containing tissue structures takes place, and additionally no thrombi are formed. On the other hand, the properties of the surfaces 14, 16 of the implant 10 allow a drastically reduced adhesion of bacteria 72 to be achieved.

Figure 16:
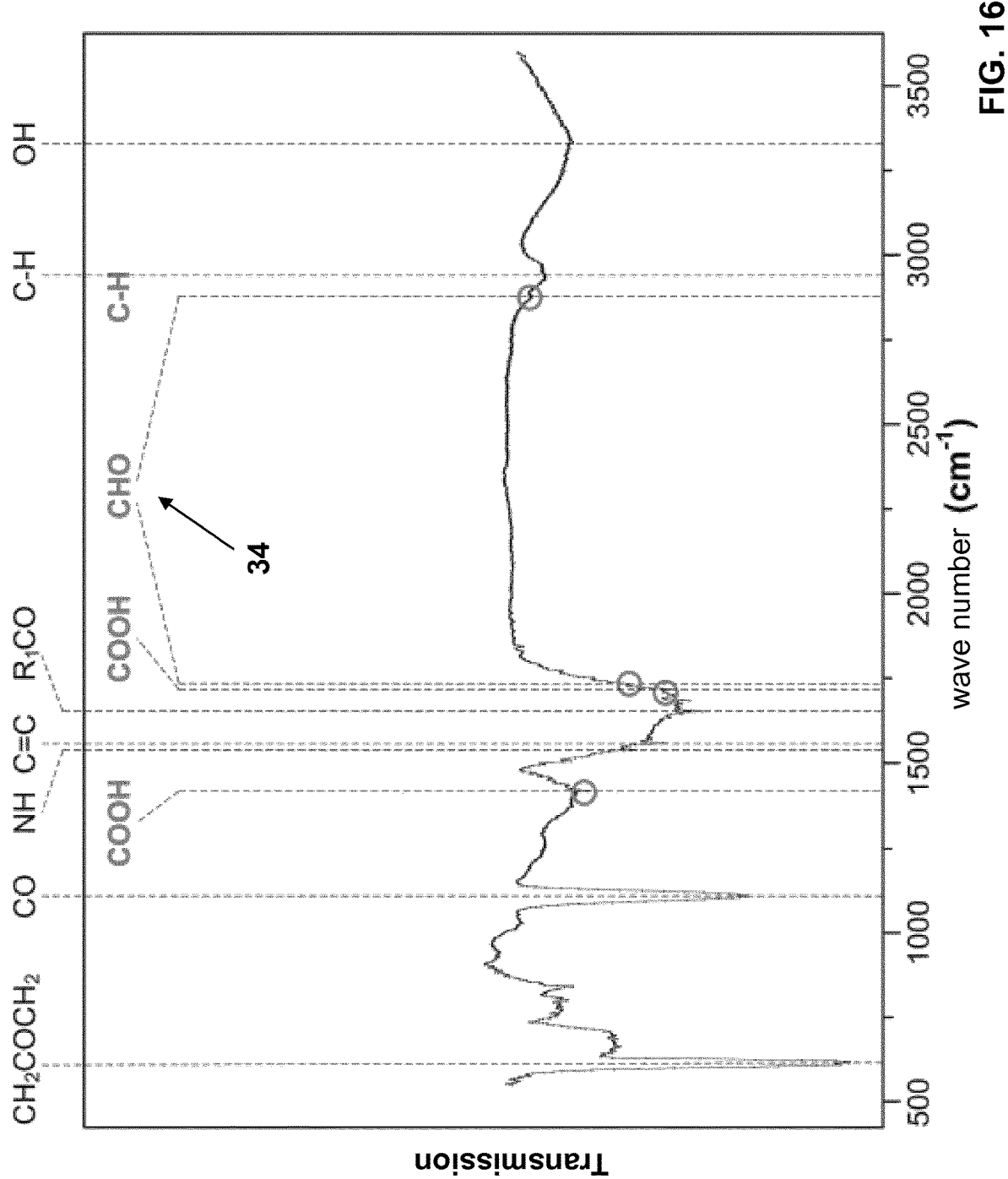
FIG. 16 shows a diagram representing a Fourier transform infrared spectroscopy of a coating according to Formulation I of FIG. 3.

To ascertain which chemical groups could be involved in the attachment of interfering substances 72, the coating 12 was examined based on a Fourier transform infrared spectroscopy. The result of the same is shown in FIG. 16, wherein here the transmission is plotted on the x axis, and the wavenumber in $cm^{-1}$ is plotted on the y axis. The aldehyde group was identified as a reactive chemical group 34 in terms of potential binding sites for non-specific adsorption.

A considerable reduction in the adsorption of interfering substances 72 can be achieved when the coating 12, 12', 12'', 12''' is treated using a treatment parameter that is selected such that reactive chemical groups 34, and more particularly aldehyde groups 34, of the coating 12 are chemically modified. In terms of the chemical modification, a reduction of the groups 34 is a good approach. Possible reducing reagents include, for example, sodium borohydride, tris(hydroxymethyl)aminomethane (TRIS), ethanolamine or glycine.

Figure 17:
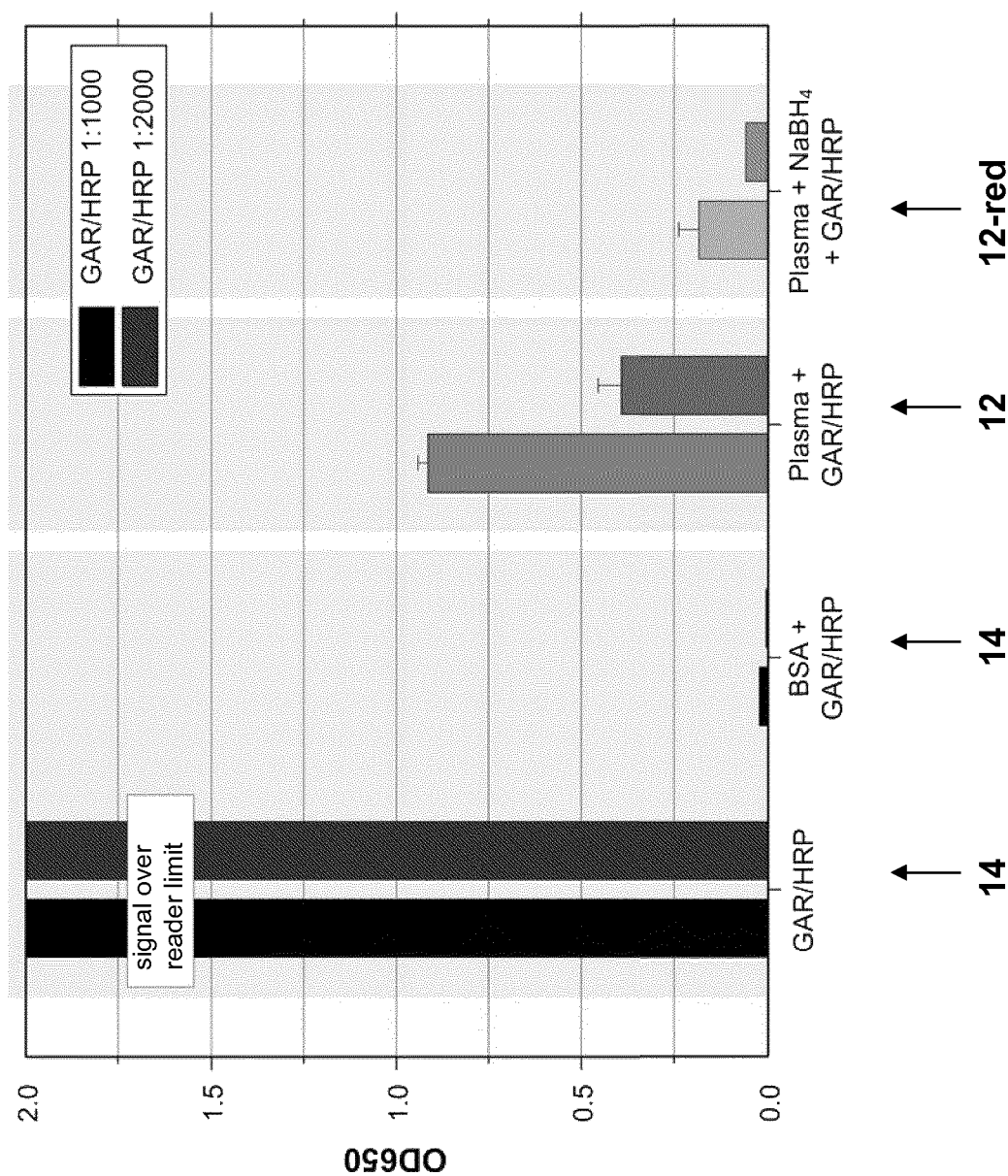
FIG. 17 shows a diagram illustrating the results of an immunoassay in which the protein adsorption as a function of a treatment of the coating according to Formulation I of FIG. 3 was examined.

For examination, the coating 12 was treated differently and then an immunoassay was carried out for analysis purposes, which shows the degree of protein adsorption on the differently treated coatings 12. The result is shown in the diagram of FIG. 17, in which a measurement signal at a wavelength of 650 nm is plotted on the x axis, and the treatment of the coating 12 is plotted on they axis.

The substrates used included uncoated and untreated surfaces 14, untreated coatings 12, and coatings 12-red reduced with sodium borohydride ($NaBH_4$), and with sodium borohydride ($NaBH_4$).

The functional principle of the immunoassay is based on the detection of binding between a substrate or a surface and a protein, in this case an antibody, which is coupled with a marker enzyme (by way of example here: antibody: goat anti-rabbit (GAR), marker enzyme: horseradish peroxidase (HRP). If the substrates are incubated with the antibody, the antibody individual adsorbs onto the substrate. Unbound antibody can be washed away using a washing step. The amount of bound GAR/HRP can now be examined by interaction with a fluorescence marker in the immunoassay. The antibody complex was used in two dilutions (1:1000, 1:2000). All incubation times were one hour. The coating time of the microtiter plate that was used was 5 minutes.

The uncoated surface 14 served as the positive control. As expected, a large amount of protein or antibodies adsorbs thereon, which is apparent from the two high measurement signals (first group of bars on the left). The approach using bovine serum albumin (BSA) is used to ascertain the background signal of the non-specific bonds of GAR/HRP with arbitrary proteins. The binding structures of the surface 14 were blocked by BSA prior to the incubation with antibodies. Since all binding structures are blocked by BSA, and only minimal accumulations of the antibody can take place, the measurement signals are low, as expected (second group of bars from left). However, the effect of the variably diluted GAR/HRP is already apparent here; the measurement signal of the left bar (dilution 1:1000) is approximately twice that of the measurement signal of the right bar (dilution 1:2000). A reduction in antibody attachment takes place in the approaches with the coating 12 (see also FIG. 6). The difference in signals for the dilutions (second group of bars from right) is also very visible here.

If the reactive chemical groups 34 of the coating 12 are now reduced using sodium borohydride (coating 12-red), the adsorption of the antibody decreases further (first group of bars from right).

It was thus possible to impressively and surprisingly demonstrate that the adsorption of interfering substances 72 onto the coating 12 can be reduced considerably, or to approximately 24% to 20%, by reducing the same, for example by way of sodium borohydride.

FIGS. 18 to 26 show two alternative exemplary embodiments of the implant 10. Identical components, features and functions are denoted by the same reference numerals. However, in order to distinguish the exemplary embodiments, the letters a and b have been added to the reference numerals in the exemplary embodiments. The description below is substantially limited to these differences compared to the exemplary embodiment of FIGS. 1 to 17, wherein reference is made to the description of the exemplary embodiment in FIGS. 1 to 17 with respect to identical components, features, and functions.

Figure 18:
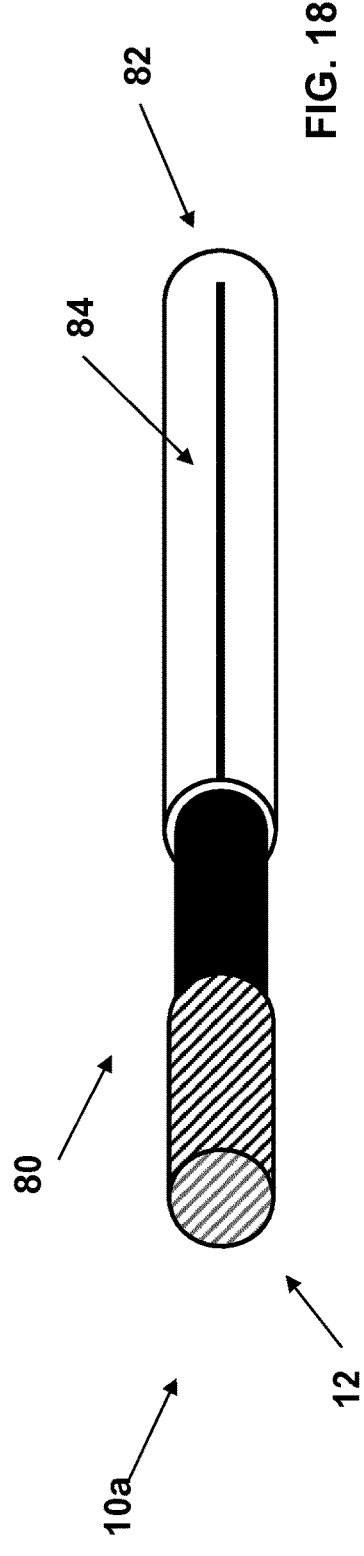
FIG. 18 shows a perspective schematic drawing of an alternative implant in the form of a model titanium cylinder, coated in the plasma polymer system of FIG. 1 with a plasma polymer layer by way of the method according to the invention, a biosensor comprising a silicone cuff, and a cable.
Figure 19:
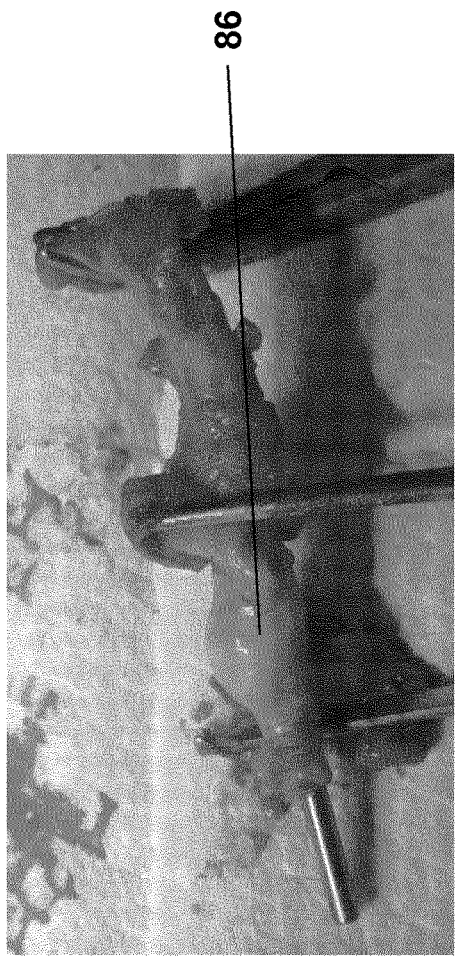
FIG. 19 shows a photograph of the implant of FIG. 18 after explantation.
Figure 20:
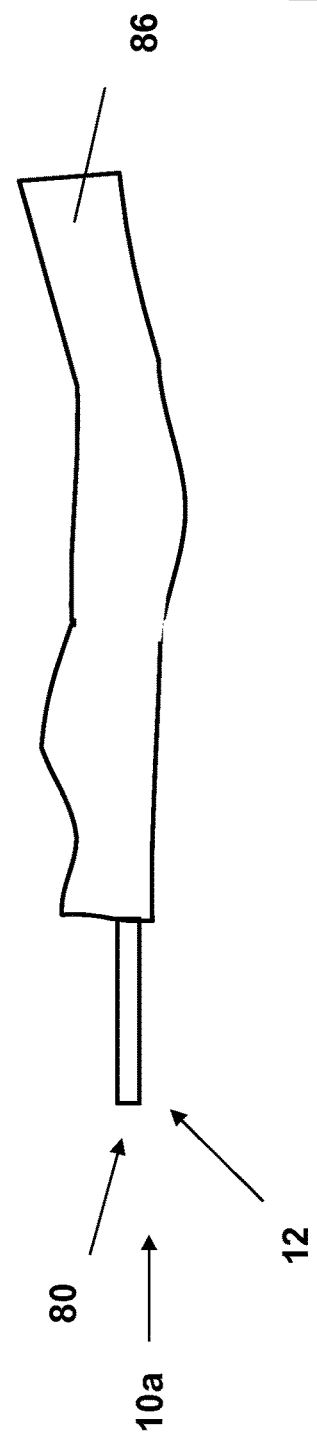
FIG. 20 shows a schematic contour drawing of the explanted implant of FIG. 19.

The implant 10a of the exemplary embodiment of FIGS. 18 to 20 differs from the implant 10 of FIGS. 1 to 17 in that it is a model of an electrical sensor comprising a housing and a cable connected thereto, which is to be introduced into a bloodstream. This may also be a biosensor.

As a model of this sensor system, an implant 10a was developed, which comprises a titanium cylinder 80 serving as the housing, having a silicone cuff 82 disposed around the rear portion of the titanium cylinder 80 (see FIG. 18, which shows the implant 10a in a perspective schematic drawing). An electrical cable 84 is embedded in the silicone cuff 82. All sections can have the same diameter or differ with respect to the diameters thereof. A front portion of the titanium cylinder 80 was coated with a coating 12 according to Formulation I using the following coating parameters: pressure: 5 Pa, flow rate of the methane coating gas 18: 2.5 sccm, flow rate of the oxygen coating gas 20: 1.3 sccm, current intensity of the plasma polymerization system: 200 mA, electrodes of the plasma polymerization system: 100% titanium, rotational speed of the sample holder 50: 2 rpm, coating time 1 min to 200 min, preferably 20 min to 100 min, and particularly preferably 60 min. The layer thickness was 20 nm.

As is apparent from FIGS. 19 and 20, which show a photograph of the implant 10a following explantation and a schematic contour drawing of the explanted implant 10a, no encapsulation of the front portion of the titanium cylinder 80, which is provided with the coating 12, takes place. The rear portion of the titanium cylinder 80 and the silicone cuff 82, in contrast, were completely encapsulated by the body of the test animal. A particularly large encapsulation 86 has even formed around the uncoated titanium of the titanium cylinder 80. This again illustrates how effective the coating 12 is.

The implant 10b of the exemplary embodiment of FIGS. 21 to 26 differs from the implant 10 of FIGS. 1 to 17 in that it is a model of a sensor system for continuously monitoring cardiovascular vital parameters. The task of this sensor system is to monitor cardiovascular parameters. This is an implantable sensor system for monitoring the blood pressure, the pulse, the pulse shape, and the oxygen saturation. The sensor is applied intracorporeally, extravasally using a highly elastic ring.

Figure 21:
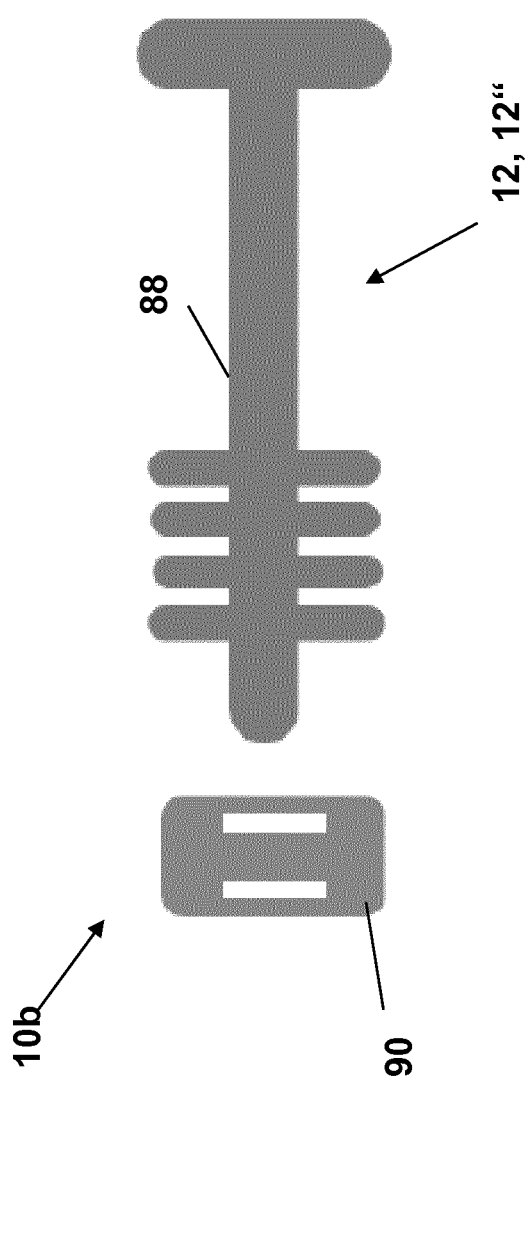
FIG. 21 shows a schematic drawing of a further alternative implant in the form of a vascular sleeve.
Figure 22:
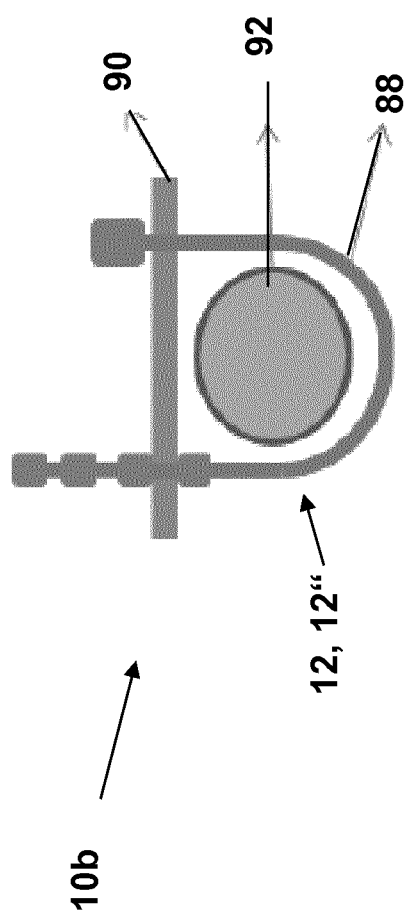
FIG. 22 shows a schematic drawing of a vascular sleeve of FIG. 21 placed around a blood vessel.
Figure 23:
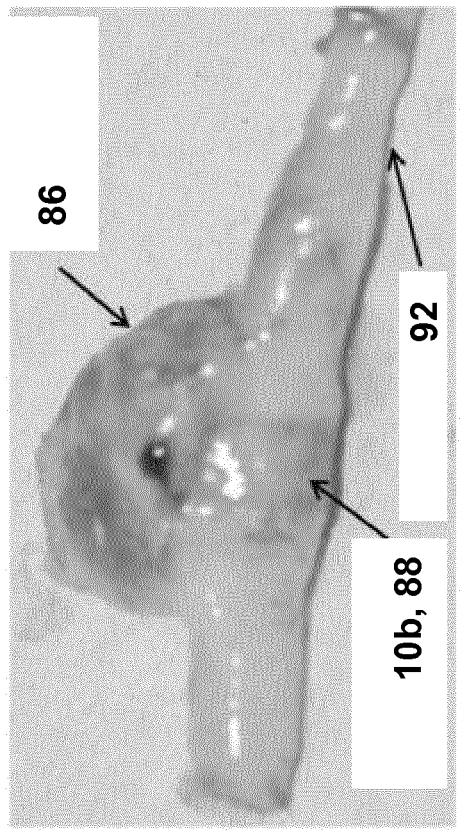
FIG. 23 shows a photograph of the uncoated implant of FIG. 22 after explantation.
Figure 24:
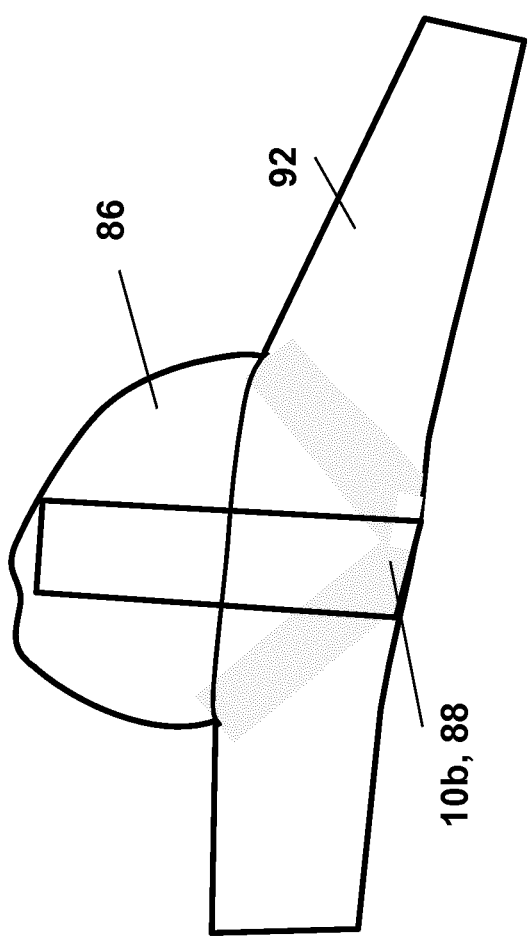
FIG. 24 shows a schematic contour drawing of the explanted implant of FIG. 23.
Figure 25:
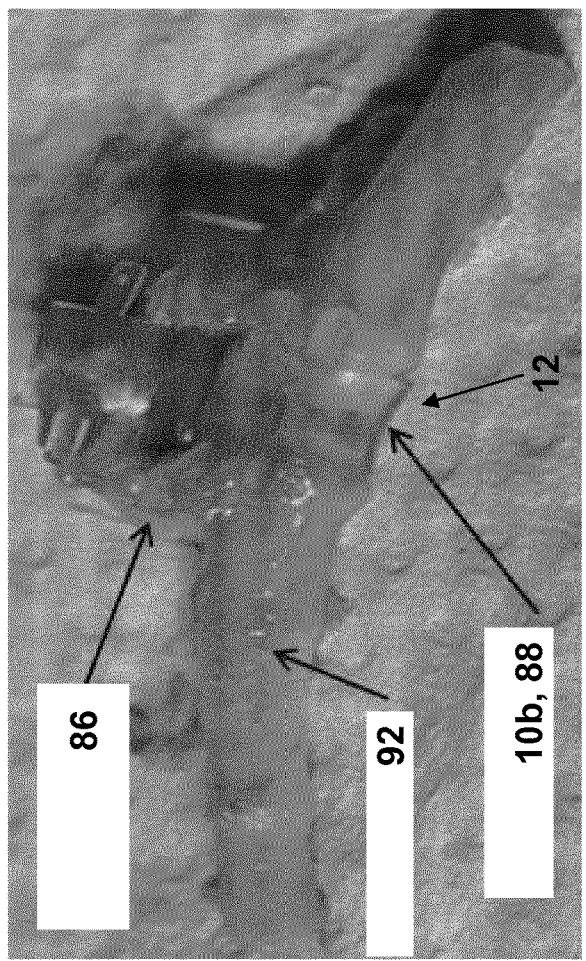
FIG. 25 shows a photograph of the implant of FIG. 22 coated in the plasma polymer system of FIG. 1 with a plasma polymer layer by way of the method according to the invention and after explantation.
Figure 26:
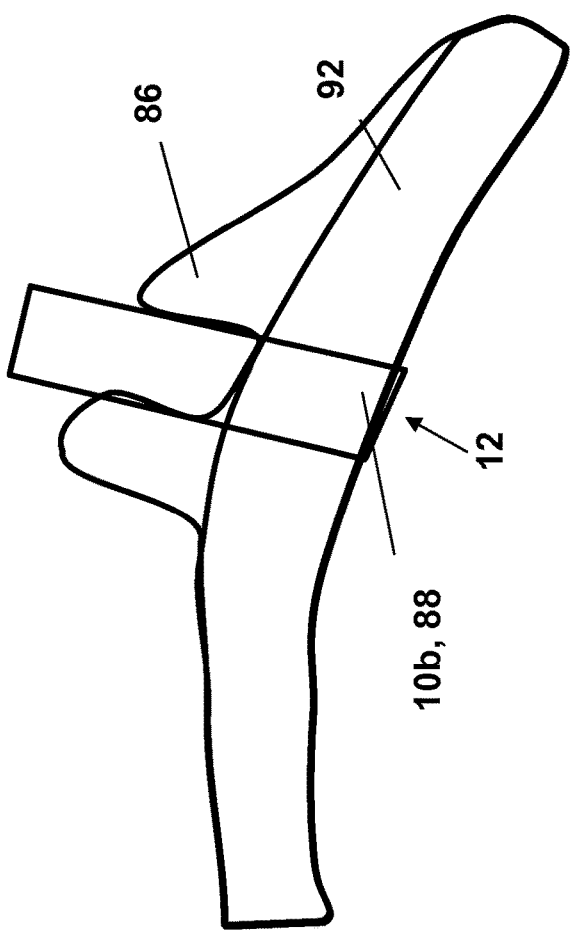
FIG. 26 shows a schematic contour drawing of the explanted implant of FIG. 25.

As a model of the sensor, an implant 10b was designed, which comprises a band-shaped silicone carrier 88, which can be closed by a Kapton closure 90 (see FIG. 21, which shows a schematic drawing of an implant 10b). As is shown in FIG. 22, the silicone carrier 88 can be placed around a blood vessel, such as an artery 92. To analyze the ingrowth behavior of the implant 10b in the body, two silicone carriers 88 were coated with coatings 12, 12" according to Formulations I and III and implanted into the tissue of test animals.

After explantation of the implants 10b, electron microscopic images of the coatings 12, 12" were created. In the case of the uncoated substrate, it can be seen that interfering substances 72 have adsorbed onto the surface, even in the form of large conglomerates. Considerably fewer interfering substances 72 have settled on the coatings 12, 12".

As is apparent from FIGS. 23 to 26, which each show photographs and schematic contour drawings of an uncoated implant 10b (FIGS. 23 and 24) and of an implant 10b coated with the coating 12 according to Formulation I (FIGS. 25 and 26) after explantation of the explanted implant 10b, the uncoated implant 10b is completely enclosed by an encapsulation 86. In contrast, if the implant 10b is coated with a coating 12, considerably less of the same is enclosed by encapsulations 86. In the case of Formulation I, the majority of the silicone carrier 88 remains free. Encapsulation 86 takes place merely in the region of the closure 90, which may be due to the uncoated polyimide. These results confirm the in vitro experiments on protein adsorption very well. The more natively the proteins adsorb on the coating 12, the less will the foreign body response will be.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

| List of reference cited | |
|---|---|
| 10 | implant |
| 12 | coating |
| 14 | surface |
| 16 | surface |
| 18 | coating gas - methane |
| 20 | coating gas - oxygen |
| 22 | plasma polymerization system |
| 24 | electrode |
| 26 | membrane |
| 28 | pore |
| 30 | layer thickness |
| 32 | adhesion promoter layer |
| 34 | group |
| 36 | functional sector |
| 38 | attachment sector |
| 40 | metal |
| 42 | stabilizer |
| 44 | magnet |
| 46 | feed system |
| 48 | reactor volume |
| 50 | sample holder |
| 52 | rotational direction |
| 54 | sensor system |
| 56 | housing |
| 58 | reservoir |
| 60 | detection system |
| 62 | receptor |
| 64 | semiconductor component |

-continued

| | List of reference cited |
|---|---|
| 66 | analyte |
| 68 | antagonist |
| 70 | diameter |
| 72 | molecule/cell/bacterium/impurity |
| 74 | micromolecule |
| 76 | binding site |
| 78 | passivation layer |
| 80 | titanium cylinder |
| 82 | silicone cuff |
| 84 | cable |
| 86 | encapsulation |
| 88 | silicone carrier |
| 90 | Kapton closure |
| 92 | artery |
| 94 | measuring unit |
| A | loading |
| B | loading |
| C | loading |
| D | loading |

What is claimed is:

1. A method for coating a medical implant, the implant comprising a membrane having pores sized in the nanometer range, the method comprising the steps of:
stabilizing the pores with at least one stabilizer; and
applying at least one coating by plasma polymerization in the presence of a coating gas and oxygen onto at least one surface of the implant and onto the membrane, wherein the plasma polymerization is carried out in the presence of at least one saturated hydrocarbon selected from the group consisting of saturated C1 to C6 hydrocarbons as the coating gas.

2. The method according to claim 1, further comprising a step of selectively removing stabilizer from a surface of the membrane by stopping supply of coating gas and subjecting the membrane to a pressure of 0.1 to 0.5 Pa for a duration: 1 min to 20 min.

3. The method according to claim 1, wherein the stabilizer is glycerol.

4. The method according to claim 1, wherein the saturated hydrocarbon is methane.

5. The method according to claim 1, wherein said applying uses the following parameters: pressure: 1 pascal (Pa) to 10 Pa, flow rate of a coating gas: 0 standard cubic centimeters per minute (sccm) to 10 sccm, current intensity of the plasma polymerization system: 100 milliamperes (mA) to 500 mA, rotational speed of the sample holder: 0 revolutions per minute (rpm) to 5 rpm, coating time: 1 minute (min) to 200 min, electrode of the plasma polymerization system: titanium, titanium content: between 50% and 100% titanium.

6. The method according to claim 1, wherein the saturated hydrocarbon is methane and wherein said applying uses the following parameters: pressure: 1 Pa, flow rate of the methane coating gas: 2.5 sccm, flow rate of the oxygen coating gas: 1.3 sccm, current intensity of the plasma polymerization system: 375 mA, electrode of the plasma polymerization system: 100% titanium.

7. The method according to claim 1, further comprising pretreating the implant by applying an adhesion promoter layer.

8. The method according to claim 1, further comprising sterilizing the coating.

9. The method according to claim 1, wherein the coating applied by said applying contains reactive chemical groups, the method further comprising reducing reactive chemical groups of the coating with a reducing reagent.

10. The method according to claim 1, further comprising covering portions of the implant during said applying to define coating-free regions prior to the plasma polymerization.

11. The method according to claim 1, wherein the plasma polymerization is conducted in the presence of at least one antibiotically acting metal.

12. The method according to claim 5, wherein the coating time is 20 min to 100 min.

13. The method according to claim 1, wherein the coating comprises a biocompatible, bioinert and antibiotic coating.

14. The method according to claim 1, wherein the coating comprises carbon, nitrogen, oxygen and a metal.

15. The method according claim 14, wherein the metal is selected from the group comprising or consisting of titanium, silver, copper, zinc, mercury, tin, lead, bismuth, cadmium, chromium, and thallium, and alloys thereof.

16. The method according to claim 14, wherein the coating is applied in a thickness of 1 nm to 200 nm.

17. The method according to claim 16, wherein the coating is applied in a thickness of 15 nm to 50 nm.

18. The method according to claim 1, wherein the implant comprises a cardiac pacemaker.

19. The method according to claim 1, wherein said applying uses the following parameters: pressure 4 Pa to 6 Pa, flow rate of methane coating gas: 3 sccm, flow rate of oxygen coating gas: 1 sccm, current intensity of the plasma polymerization system: 150 mA to 250 mA, coating time: 30 min to 200 min, electrode of the plasma polymerization system: titanium, titanium content: 100%.

* * * * *